US012247975B2

(12) United States Patent
Horii et al.

(10) Patent No.: US 12,247,975 B2
(45) Date of Patent: Mar. 11, 2025

(54) DETECTION APPARATUS AND DETECTION METHOD

(71) Applicant: Sysmex Corporation, Kobe (JP)

(72) Inventors: Kazuyoshi Horii, Kobe (JP); Tomoyuki Nose, Kobe (JP); Takao Fujiwara, Kobe (JP); Sayuri Tomoda, Kobe (JP); Yusuke Miida, Kobe (JP); Yasunori Maekawa, Kobe (JP); Noriaki Sasaki, Kobe (JP)

(73) Assignee: Sysmex Corporation, Kobe (JP)

( * ) Notice: Subject to any disclaimer, the term of this patent is extended or adjusted under 35 U.S.C. 154(b) by 688 days.

(21) Appl. No.: 17/162,443

(22) Filed: Jan. 29, 2021

(65) Prior Publication Data
US 2021/0148905 A1 May 20, 2021

Related U.S. Application Data

(63) Continuation of application No. 15/637,957, filed on Jun. 29, 2017, now Pat. No. 11,099,182.

(30) Foreign Application Priority Data

Jun. 30, 2016 (JP) .................................. 2016-130097
Sep. 13, 2016 (JP) .................................. 2016-179029

(51) Int. Cl.
*G01N 33/543* (2006.01)
*B01L 3/00* (2006.01)
(Continued)

(52) U.S. Cl.
CPC .. *G01N 33/54326* (2013.01); *B01L 3/502761* (2013.01); *B03C 1/284* (2013.01);
(Continued)

(58) Field of Classification Search
CPC .. G01N 33/54326; G01N 21/69; G01N 21/76; G01N 33/582; G01N 35/00069;
(Continued)

(56) References Cited

U.S. PATENT DOCUMENTS

2003/0146155 A1    8/2003 Tooke et al.
2008/0035579 A1*   2/2008 Lee .................. G01N 35/00069
                                                210/695
(Continued)

FOREIGN PATENT DOCUMENTS

CN         105229449          1/2016
WO    WO-2016051795 A1 *      4/2016  .............. B01L 3/502

OTHER PUBLICATIONS

Chinese Office Action issued on Mar. 13, 2024 in a counterpart Chinese patent application No. 202110939937.5.

*Primary Examiner* — Jill A Warden
*Assistant Examiner* — Jacqueline Brazin
(74) *Attorney, Agent, or Firm* — Crowell & Moring LLP

(57) ABSTRACT

Disclosed is a detection apparatus that transfers magnetic particles through a plurality of chambers in a cartridge which includes the plurality of chambers and a channel connecting between the plurality of chambers, and that causes the magnetic particles to carry a complex of a test substance and a labelling substance, to detect the test substance on the basis of the labelling substance in the complex. The detection apparatus includes: a rotation mechanism configured to rotate the cartridge about a rotation shaft; a magnet configured to collect the magnetic particles in the chambers; a movement mechanism configured to move the magnet in a direction different from a circumferential direction of a circle in which the rotation shaft is centered; a detector configured to detect the test substance; and a controller programmed to control the rotation mechanism (Continued)

and the movement mechanism so as to transfer the magnetic particles from one of the chambers to another one of the chambers.

10 Claims, 25 Drawing Sheets

(51) Int. Cl.
- *B03C 1/28* (2006.01)
- *G01N 21/69* (2006.01)
- *G01N 21/76* (2006.01)
- *G01N 33/58* (2006.01)
- *G01N 35/00* (2006.01)
- *G01N 35/10* (2006.01)

(52) U.S. Cl.
CPC .............. *G01N 21/69* (2013.01); *G01N 21/76* (2013.01); *G01N 33/582* (2013.01); *G01N 35/00069* (2013.01); *G01N 35/0098* (2013.01); *G01N 35/10* (2013.01); *B01L 2200/0668* (2013.01)

(58) Field of Classification Search
CPC .............. G01N 35/0098; G01N 35/10; G01N 2035/00495; G01N 2035/00574; G01N 33/532; G01N 35/04; G01N 2035/0439; B01L 3/502761; B01L 2200/0668; B01L 2300/0803; B01L 2300/0858; B01L 2300/0864; B01L 2300/087; B01L 2400/0409; B01L 2400/043; B03C 1/284
USPC ....................................................... 422/509
See application file for complete search history.

(56) References Cited

U.S. PATENT DOCUMENTS

| | | |
|---|---|---|
| 2008/0171400 A1 | 7/2008 | Cho et al. |
| 2010/0129878 A1* | 5/2010 | Parthasarathy ...... C12Q 1/6806 435/91.5 |
| 2010/0135859 A1 | 6/2010 | Sa |
| 2013/0206701 A1* | 8/2013 | Strohmeier ............... B03C 1/02 210/695 |
| 2015/0005188 A1* | 1/2015 | Levner ................. C12Q 1/6804 506/9 |
| 2016/0061831 A1* | 3/2016 | Nobuki .................. G01N 21/69 422/52 |
| 2016/0320375 A1* | 11/2016 | Horii ..................... B01F 31/441 |

* cited by examiner

CROSS-SECTION C1-C2

CROSS-SECTION C1-C2

CROSS-SECTION C1-C2

CROSS-SECTION C3-C4

DETECTION APPARATUS AND DETECTION METHOD

CROSS REFERENCE TO RELATED APPLICATIONS

This application is a continuation application of non-provisional U.S. patent application Ser. No. 15/637,957, filed on Jun. 29, 2017, which claims priority from prior Japanese Patent Application Nos. 2016-130097, filed on Jun. 30, 2016, and 2016-179029, filed Sep. 13, 2016, the entire content of which is incorporated herein by reference.

FIELD OF THE INVENTION

The present invention relates to a detection apparatus and a detection method for performing detection of a test substance.

BACKGROUND

A method in which magnetic particles are transferred from a chamber of a cartridge to a chamber adjacent thereto by using a magnetic force, and a centrifugal force that is generated by rotation of a disk, is disclosed in U.S. Pat. No. 8,951,417 (hereinafter, referred to as Patent Literature 1).

Specifically, as shown in FIG. 25A, a rotational body typified by a disk includes two chambers 611, 612 adjacent to each other. The chambers 611, 612 are connected by a connecting portion 613 disposed on the inner circumferential side of the rotational body. The rotational body is rotated in a state shown in FIG. 25A, and a magnet 620 is located at a position, in the connecting portion 613, which connects to the chamber 611 as shown in FIG. 25B. The magnet 620 is fixed above the rotational body. The magnet 620 attracts magnetic particles 630 stored in the chamber 611, from the chamber 611 toward the connecting portion 613. Subsequently, the rotational body is rotated at a low speed, and the magnetic particles 630 attracted by the magnet 620 are moved to a position, in the connecting portion 613, corresponding to the chamber 612 as shown in FIG. 25C. Thereafter, the rotational body is rotated at a high speed, and the magnetic particles 630 are moved from the connecting portion 613 into the chamber 612 by a centrifugal force as shown in FIG. 25D.

In the method disclosed in Patent Literature 1, the magnetic particles 630 stored in the chamber 611 are attracted toward the connecting portion 613 by a magnetic force of the magnet 620. Therefore, some of the magnetic particles 630 may be left in the chamber 611 while the magnetic particles 630 are moved toward the connecting portion 613. The longer a distance between the magnet 620 and the magnetic particle 630 is, the lower a magnetic force exerted from the magnet 620 onto the magnetic particle 630 is. Therefore, a magnetic force is not sufficiently exerted from the magnet 620 onto the magnetic particles 630 positioned so as to be distant from the magnet 620, and the magnetic particles 630 may be left in the chamber 611. Thus, if the magnetic particles are left in the chamber, a part of a test substance that is bound to the magnetic particles is not detected, resulting in reduction of detection accuracy for the test substance.

SUMMARY OF THE INVENTION

The scope of the present invention is defined solely by the appended claims, and is not affected to any degree by the statements within this summary.

A first mode of the present invention is a detection apparatus that transfers magnetic particles through a plurality of chambers in a cartridge which includes the plurality of chambers and a channel connecting between the plurality of chambers, and that causes the magnetic particles to carry a complex of a test substance and a labelling substance, to detect the test substance on the basis of the labelling substance in the complex. The detection apparatus according to this mode includes: a rotation mechanism configured to rotate the cartridge about a rotation shaft; a magnet configured to collect the magnetic particles in the chambers; a movement mechanism configured to move the magnet in a direction different from a circumferential direction of a circle in which the rotation shaft is centered; a detector configured to detect the test substance; and a controller programmed to control the rotation mechanism and the movement mechanism so as to transfer the magnetic particles from one of the chambers to another one of the chambers.

In the detection apparatus according to this mode, the cartridge is a replaceable component that collectively has functions required for detection of a test substance. The chamber is a storage portion that is provided in the cartridge for storing a sample prepared from the test substance and a predetermined reagent. The chamber may not constantly store liquid, and the chamber is merely required to be spatially spread for storing liquid. The channel is a passage provided in the cartridge for transferring the magnetic particles. The rotation mechanism includes, for example, a motor, and drives the motor to rotate the cartridge. The magnet includes, for example, a permanent magnet. The movement mechanism includes, for example, a motor, and drives the motor to move the magnet. The detector includes, for example, a light detector. The controller includes, for example, a processing unit and a storage unit. When only the movement mechanism, among the rotation mechanism and the movement mechanism, is driven, a position of the magnet and a position of the cartridge are changed relative to each other in a direction different from the circumferential direction. When only the rotation mechanism, among the rotation mechanism and the movement mechanism, is driven, a position of the magnet and a position of the cartridge are changed relative to each other in the circumferential direction.

A second mode of the present invention is a detection method for transferring magnetic particles through a plurality of chambers, and causing the magnetic particles to carry a complex of a test substance and a labelling substance, to detect the test substance on the basis of the labelling substance in the complex. The detection method according to this mode includes rotating, about a rotation shaft, a cartridge including the plurality of chambers and a channel that connects between the plurality of chambers, moving a magnet in a direction different from a circumferential direction of a circle in which the rotation shaft is centered, and thus transferring the magnetic particles from one of the chambers to another one of the chambers, to detect the test substance.

A third mode of the present invention is a detection apparatus that transfers magnetic particles through a plurality of chambers in a cartridge which includes the plurality of chambers and a channel connecting between the plurality of chambers, and that causes the magnetic particles to carry a complex of a test substance and a labelling substance, to detect the test substance on the basis of the labelling substance in the complex. The detection apparatus according to this mode includes: a rotation mechanism configured to rotate the cartridge about a rotation shaft; a magnet configured to collect the magnetic particles in the chambers; a movement mechanism configured to move the cartridge in a direction different from a circumferential direction of a circle in which the rotation shaft is centered; a detector configured to detect the test substance; and a controller programmed to control the rotation mechanism and the movement mechanism so as to transfer the magnetic particles from one of the chambers to another one of the chambers.

DETAILED DESCRIPTION OF THE PREFERRED EMBODIMENTS

Embodiment 1

Outlines of a detection apparatus and a cartridge according to Embodiment 1 will be described with reference to FIGS. 1A, 1B.

Figure 1A:
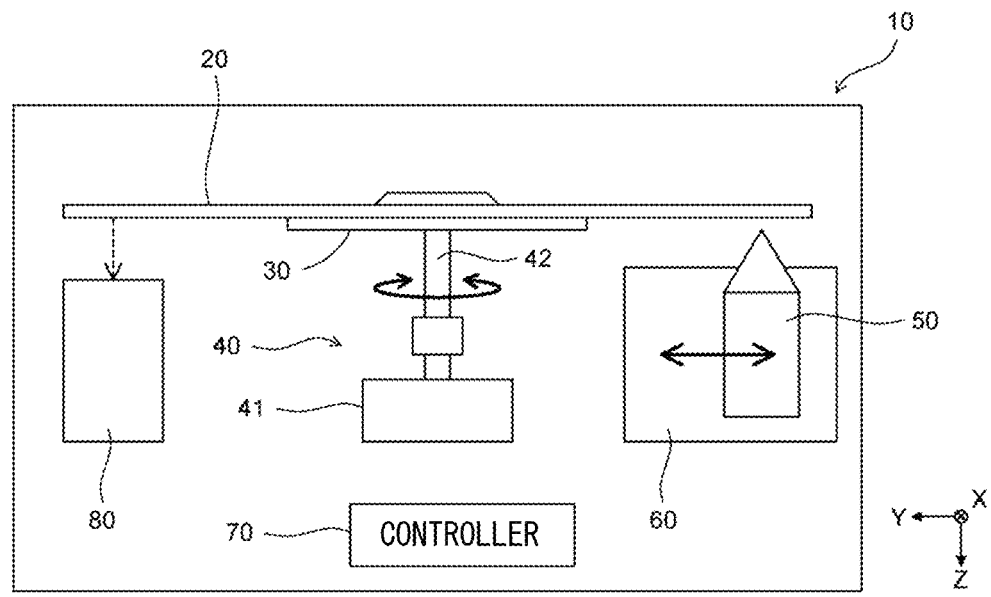
FIG. 1A is a schematic diagram illustrating a structure of a detection apparatus according to an outline of Embodiment 1.

As shown in FIG. 1A, a detection apparatus 10 causes magnetic particles to be transferred sequentially into a plurality of chambers, causes the magnetic particles to carry a test substance and a labelling substance, and detects the test substance on the basis of the labelling substance. The detection apparatus 10 includes a support member 30, a rotation mechanism 40, a magnet 50, a movement mechanism 60, a controller 70, and a detector 80. In FIG. 1A, the XYZ-axes are orthogonal to each other. An X-axis positive direction represents a rearward direction, a Y-axis positive direction represents a leftward direction, and a Z-axis positive direction represents the vertically downward direction.

On the support member 30, a cartridge 20 is placed. The rotation mechanism 40 includes a motor 41 and a rotation shaft 42. The rotation shaft 42 extends in the vertical direction. The upper end of the rotation shaft 42 is fixed by the support member 30, and the lower end of the rotation shaft 42 is fixed to a driving shaft of the motor 41. The rotation mechanism 40 drives the motor 41, and rotates the cartridge 20 placed on the support member 30, about the rotation shaft 42. Hereinafter, the radial direction and the circumferential direction of a circle around the rotation shaft 42 are simply referred to as "radial direction" and "circumferential direction", respectively.

Figure 1B:
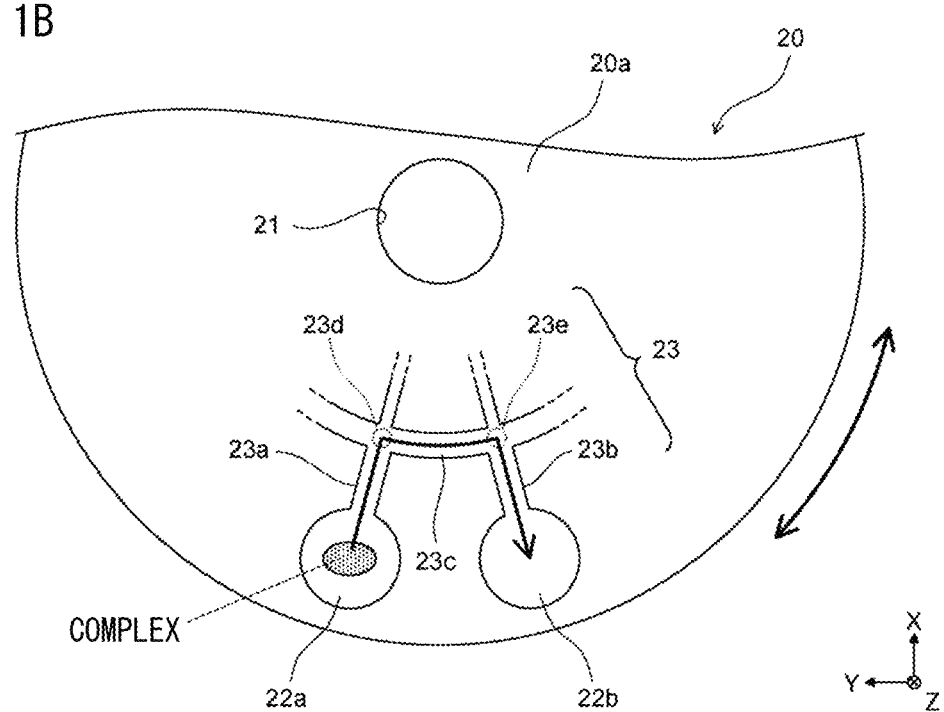
FIG. 1B is a schematic diagram illustrating a structure of a cartridge according to the outline of Embodiment 1.

As shown in FIG. 1B, the cartridge 20 is a replaceable component that collectively has functions required for detection of a test substance. The cartridge 20 includes a first chamber 22a, a second chamber 22b, and a channel 23. The cartridge 20 is formed by a substrate 20a that is plate-shaped and disk-shaped. The cartridge 20 may not be plate-shaped and may include a protrusion or the like, and may not be disk-shaped and may have another shape such as a rectangular shape.

The substrate 20a has a hole 21, the first chamber 22a, the second chamber 22b, and the channel 23 formed therein. The hole 21 penetrates through the substrate 20a at the center of the substrate 20a. The cartridge 20 is placed at the detection apparatus 10 such that the center of the hole 21 is aligned with the rotation shaft 42.

The first chamber 22a and the second chamber 22b are each a storage portion that is provided in the cartridge 20 for storing a sample prepared from the test substance and a predetermined reagent. The first chamber 22a and the second chamber 22b may not constantly store liquid, and each of the first chamber 22a and the second chamber 22b is merely required to be spatially spread for storing liquid. The channel 23 is a passage provided in the cartridge 20 for transferring the magnetic particles.

The first chamber 22a and the second chamber 22b are disposed so as to be aligned in the circumferential direction. For example, the first chamber 22a stores a complex in which a test substance, the magnetic particles, and a labelling substance bind to each other. The channel 23 extends from the rotation shaft 42 side and connects to the first chamber 22a and the second chamber 22b, and connects between the first chamber 22a and the second chamber 22b.

The channel 23 includes a first region 23a, a second region 23b, and a third region 23c. The first region 23a extends in the radial direction, and connects to the first chamber 22a. The second region 23b extends in the radial direction, and connects to the second chamber 22b. The third region 23c extends in the circumferential direction. Both ends of the third region 23c connect to the first region 23a and the second region 23b. The first region 23a and the third region 23c connect to each other at a connecting portion 23d. The second region 23b and the third region 23c connect to each other at a connecting portion 23e. In the example shown in FIG. 1B, the first chamber 22a and the second chamber 22b each has a liquid phase region for storing liquid. The channel 23 has a gas phase region for storing gas.

Both ends of the third region 23c may not necessarily be connected to the first region 23a and the second region 23b. For example, the third region 23c that connects to the first region 23a and the third region 23c that connects to the second region 23b may be separately provided, and a channel therebetween may be curved so as to be U-shaped. A liquid phase region may be provided in the channel that is curved so as to be U-shaped. The first region 23a and the second region 23b may extend, in a horizontal plane, in directions that deviate from the radial direction and are different from the circumferential direction. The first region 23a and the second region 23b may not be provided, and the first chamber 22a and the second chamber 22b may connect directly to the third region 23c.

Returning to FIG. 1A, the magnet 50 acts so as to collect the magnetic particles that spread in the first chamber 22a. To the magnetic particles in the first chamber 22a, the test substance and the labelling substance are bound as described above. The magnet 50 may be implemented as a permanent magnet, or may be implemented as an electromagnet. The movement mechanism 60 moves the magnet 50 in the horizontal plane in a direction different from the circumferential direction. Specifically, the movement mechanism 60 moves the magnet 50 in the radial direction. The movement mechanism 60 moves the magnet 50 in the vertical direction. That is, the movement mechanism 60 moves the magnet 50 so as to be close to the rotation shaft 42 and distant from the rotation shaft 42, and moves the magnet 50 so as to be close to the cartridge 20 and distant from the cartridge 20.

In a case where the first region 23a and the second region 23b extend in the directions that deviate from the radial direction, the movement mechanism 60 moves the magnet 50 in the direction that deviates from the radial direction. The movement mechanism 60 may move the magnet 50 in the direction that deviates from the vertical direction when the magnet 50 is moved so as to be close to the cartridge 20 and distant from the cartridge 20.

The movement mechanism 60 is merely required to change a position of the magnet 50 and a position of the cartridge 20 relative to each other. For example, the movement mechanism 60 may move the cartridge 20 by moving the support member 30 that supports the cartridge 20, to move the magnet 50 relative to the cartridge 20. In a case where the support member 30 is moved, a component for moving the support member 30 needs to be separately provided. Therefore, the size of the detection apparatus 10 may be increased. Accordingly, the magnet 50 is preferably moved relative to the cartridge 20 without moving the support member 30.

The controller 70 controls the rotation mechanism 40 and the movement mechanism 60. The controller 70 drives the movement mechanism 60 to move the magnet 50 so as to be close to the cartridge 20 at a position opposing the first chamber 22a, and collects the magnetic particles in the complex by a magnetic force of the magnet 50. Thereafter, the controller 70 causes the magnet 50 to be maintained close to the cartridge 20 until the magnetic particles are moved into the second chamber 22b.

The controller 70 causes the magnet 50 to be moved in the radial direction from the position opposing the first chamber 22a, and thus causes the magnetic particles collected by the magnet 50 in the first chamber 22a to be moved from the first chamber 22a into the channel 23. Subsequently, the controller 70 causes the cartridge 20 to be rotated and causes the magnetic particles collected by the magnet 50 to be moved in the channel 23. Subsequently, the controller 70 causes the magnet 50 to be moved in the radial direction from the position opposing the channel 23, and thus causes the magnetic particles collected by the magnet 50 to be moved from the channel 23 into the second chamber 22b. When the magnetic particles are transferred from the first chamber 22a into the second chamber 22b, the magnetic particles are transferred from the liquid phase region of the first chamber 22a through the gas phase region of the channel 23 into the liquid phase region of the second chamber 22b.

Specifically, the controller 70 drives the movement mechanism 60 to move the magnet 50 so as to be close to the rotation shaft 42, whereby the magnetic particles in the first chamber 22a are moved through the first region 23a to the connecting portion 23d. Subsequently, the controller 70 drives the rotation mechanism 40 to rotate the cartridge 20, whereby the magnetic particles positioned at the connecting portion 23d are moved through the third region 23c to the connecting portion 23e. The controller 70 drives the movement mechanism 60 to move the magnet 50 so as to be distant from the rotation shaft 42, whereby the magnetic particles positioned at the connecting portion 23e are moved through the second region 23b into the second chamber 22b.

When the magnetic particles positioned at the connecting portion 23d are moved to the connecting portion 23e, the rotation mechanism 40 is merely required to move the magnet 50 relative to the cartridge 20. For example, the rotation mechanism 40 may move the magnet 50 in the circumferential direction. However, when the magnet 50 is moved in the circumferential direction, a component for moving the magnet 50 in the circumferential direction needs to be separately provided. Therefore, the size of the detection apparatus 10 may be increased. Accordingly, the cartridge 20 is preferably rotated in the circumferential direction without moving the magnet 50. Also when the cartridge 20 includes three or more chambers, the controller 70 causes the magnetic particles to be transferred sequentially into the plurality of chambers as described above.

The detector 80 detects light generated by reaction in the second chamber 22b. The controller 70 analyzes the test substance on the basis of the light detected by the detector 80.

In the detection apparatus 10 as described above, when the magnet 50 is moved so as to be close to the cartridge 20 at the position opposing the first chamber 22a, a distance between the magnetic particles and the magnet 50 is shortened at any position in the first chamber 22a. Therefore, a magnetic force can be sufficiently exerted onto all the magnetic particles in the first chamber 22a, and the magnetic particles in the first chamber 22a can be assuredly collected at the position of the magnet 50. The magnetic particles collected in the first chamber 22a are moved into the second chamber 22b through the channel 23 according to movement of the magnet 50. Therefore, the collected magnetic particles can be assuredly moved to the channel 23 without leaving the magnetic particles in the first chamber 22a.

<Specific Example of Structure>

Hereinafter, specific structures of an analyzer and a cartridge according to Embodiment 1 will be described.

An analyzer 100 corresponds to the detection apparatus 10 shown in FIG. 1A. A support member 177 corresponds to the support member 30 shown in FIG. 1A. A rotation mechanism that includes a rotation shaft 311, a motor 171, and a fixing member 312 corresponds to the rotation mechanism 40 shown in FIG. 1A. The motor 171 corresponds to the motor 41 shown in FIG. 1A. The rotation shaft 311 corresponds to the rotation shaft 42 shown in FIG. 1A. A magnet 120 corresponds to the magnet 50 shown in FIG. 1A. A movement mechanism 130 corresponds to the movement mechanism 60 shown in FIG. 1A. A controller 301 corresponds to the controller 70 shown in FIG. 1A. A detector 140 corresponds to the detector 80 shown in FIG. 1A. A cartridge 200 corresponds to the cartridge 20 shown in FIG. 1B.

Figure 2A:
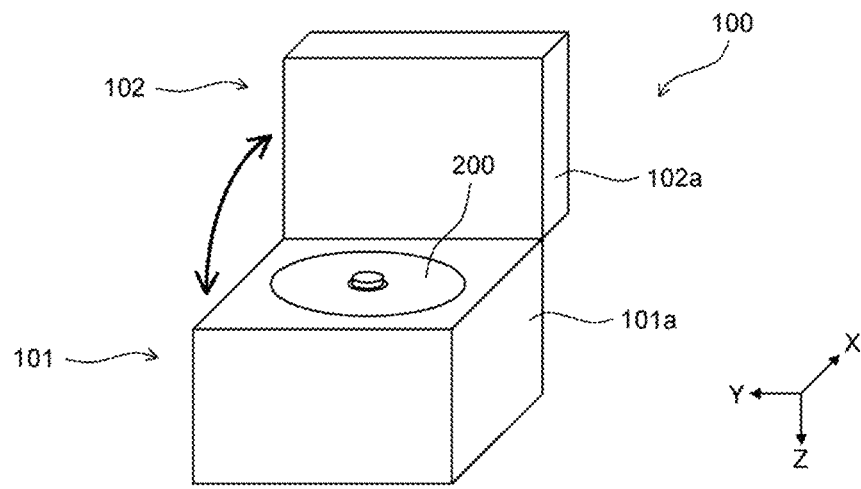
FIG. 2A is a schematic diagram illustrating an external structure of an analyzer according to Embodiment 1.

As shown in FIG. 2A, the analyzer 100 is an immune analyzer that detects a test substance in a specimen by utilizing antigen-antibody reaction, and analyzes the test substance on the basis of the detection result. The analyzer 100 includes a body portion 101 and a lid portion 102. Portions, of the body portion 101, other than a portion opposing the lid portion 102 are covered by a casing 101a. Portions, of the lid portion 102, other than a portion opposing the body portion 101 are covered by a casing 102a. The body portion 101 supports the lid portion 102 such that the lid portion 102 is openable and closable. When the cartridge 200 is attached or detached, the lid portion 102 is opened as shown in FIG. 2A. The cartridge 200 is placed at the upper portion of the body portion 101.

Figure 2B:
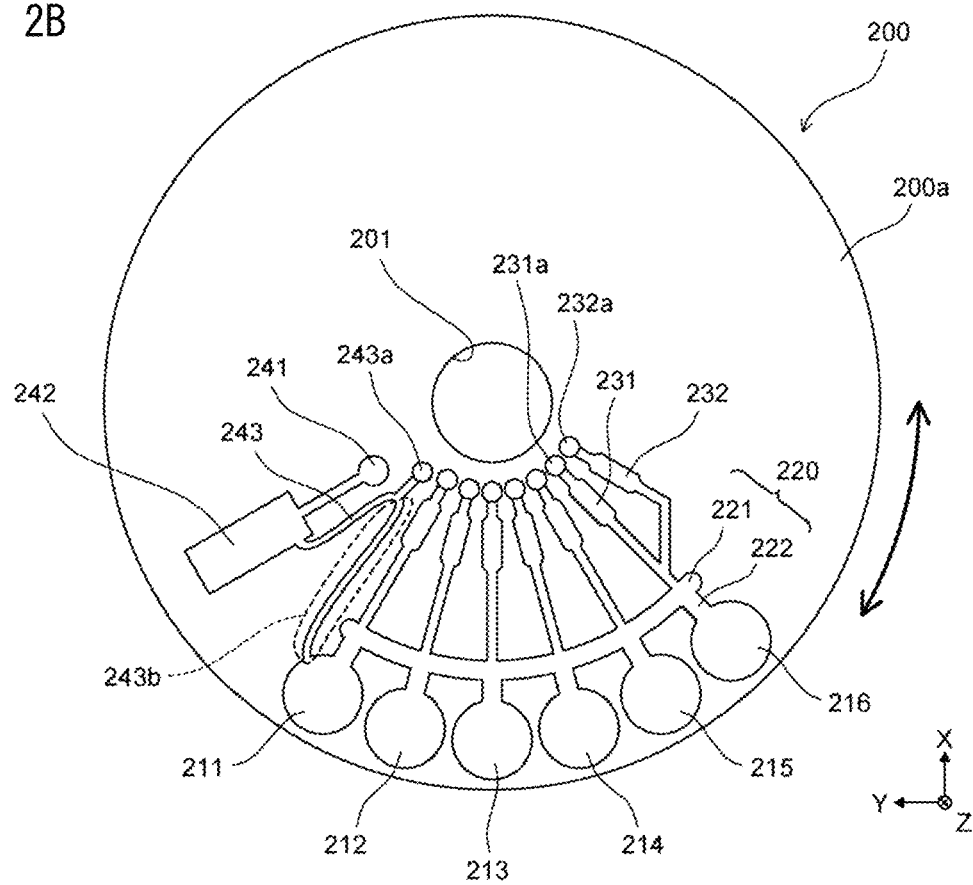
FIG. 2B is a schematic diagram illustrating a structure of a cartridge according to Embodiment 1 as viewed from thereabove.

As shown in FIG. 2B, the cartridge 200 is formed by a substrate 200a that is plate-shaped and disk-shaped. Components in the cartridge 200 are each formed by a not-illustrated film that covers the entire surface of the substrate 200a being adhered over a recess formed in the substrate 200a. The substrate 200a and the film adhered to the substrate 200a are formed from translucent members. The substrate 200a has such a thickness as to facilitate adjustment of a temperature of the cartridge 200 by heaters 321, 322 described below. For example, the thickness of the substrate 200a is several millimeters, and is specifically 1.2 mm.

The substrate 200a includes a hole 201, chambers 211 to 216, a channel 220, six liquid storage portions 231, a liquid storage portion 232, an opening 241, a separator 242, and a channel 243. The hole 201 penetrates through the substrate 200a at the center of the substrate 200a. The cartridge 200 is placed at the analyzer 100 such that the center of the hole 201 is aligned with the rotation shaft 311 described below. Hereinafter, the radial direction and the circumferential direction of a circle around the rotation shaft 311 are simply referred to as "radial direction" and "circumferential direction", respectively. The chambers 211 to 216 are aligned in the circumferential direction near the outer circumference of the substrate 200a.

The channel 220 includes an arc-like region 221 that extends in the circumferential direction, and six regions 222 that extend in the radial direction. The region 221 connects to the six regions 222. The six regions 222 connect to the chambers 211 to 216, respectively. The six liquid storage portions 231 connect to the channel 220 through flow paths and are disposed on extensions of the regions 222 that connect to the chambers 211 to 216, respectively. The liquid storage portion 232 connects through a flow path to a flow path that connects between the region 222 that connects to the chamber 216, and the liquid storage portion 231 on the extension of the region 222 that connects to the chamber 216.

The liquid storage portion 231 stores a reagent and has a seal 231a on the upper surface on the inner side in the radial direction. The seal 231a can be opened when pressed from thereabove by a pressing portion 195 described below. Before the seal 231a is opened, the reagent in the liquid storage portion 231 does not flow into the channel 220, and when the seal 231a is opened, the inside of the liquid storage portion 231 is in communication with the channel 220, and the reagent in the liquid storage portion 231 flows into the channel 220. Specifically, when the seal 231a is opened, the inside of the liquid storage portion 231 connects to the outside of the cartridge 200 at the position of the seal 231a.

Similarly, the liquid storage portion 232 stores a reagent and has a seal 232a on the upper surface on the inner side in the radial direction. The seal 232a can be opened when pressed from thereabove by the pressing portion 195. Before the seal 232a is opened, the reagent in the liquid storage portion 232 does not flow into the channel 220, and when the seal 232a is opened, the inside of the liquid storage portion 232 is in communication with the channel 220, and the reagent in the liquid storage portion 232 flows into the channel 220. Specifically, when the seal 232a is opened, the inside of the liquid storage portion 232 connects to the outside of the cartridge 200 at the position of the seal 232a.

The seals 231a, 232a may be integrated with the substrate 200a, or may be each formed by, for example, a film adhered over an opening formed in the substrate 200a.

A blood specimen of whole blood collected from a subject is injected into the separator 242 through the opening 241. The blood specimen injected into the separator 242 is separated into blood cells and plasma in the separator 242. The plasma separated in the separator 242 is moved into the channel 243. A hole 243a is formed on the upper surface on the inner side, in the radial direction, of the channel 243. The plasma positioned in a region 243b of the channel 243 is moved into the chamber 211 by a centrifugal force when the cartridge 200 is rotated. Thus, a predetermined amount of plasma is transferred into the chamber 211.

The components of the substrate 200a are provided in only one-third of the region of the substrate 200a as shown in FIG. 2B. However, the structure is not limited thereto, and a group of the components may be provided in the remaining two-thirds of the region of the substrate 200a, and three groups of the components may be provided in the substrate 200a.

Subsequently, an internal structure of the analyzer 100 will be described with reference to FIG. 3 to FIG. 12B.

A mounting member 110 has holes 111 to 114 formed therein. The holes 111 to 114 penetrate through the mounting member 110. In the hole 111, the rotation shaft 311 described below is positioned. The hole 112 is elongated in the radial direction. The movement mechanism 130 is mounted on the lower surface of the mounting member 110 through a member 131. In the horizontal plane, a hole 131a of the member 131 is aligned in position with the hole 112 of the mounting member 110. The detector 140 is mounted on the lower surface of the mounting member 110 through a member 141. In the horizontal plane, a reflector 142 of the detector 140 is aligned in position with the hole 113 of the mounting member 110. In the hole 114, a temperature sensor 178 described below is mounted. Protrusions 115, 116 which are each shaped into a closed-loop are formed on the upper surface of the mounting member 110. The protrusions 115, 116 protrude upward along the circumferential direction.

A housing unit 150 has an upper surface 151, housings 152, 153, and an outer surface 154. At the center of the upper surface 151, a hole 155 is formed so as to penetrate through the upper surface 151 to the outer surface 154 in the up-down direction. The hole 155 allows the rotation shaft 311 described below to pass therethrough. The housings 152, 153 are formed as recesses that are recessed downward from the upper surface 151. The mounting member 110 having the movement mechanism 130 and the detector 140 mounted thereto is mounted in the housing unit 150. When the mounting member 110 is mounted in the housing unit 150, the lower surface of the outer perimeter of the mounting member 110 and the upper surface of the outer perimeter of the housing unit 150 are jointed to each other. When the mounting member 110 is mounted in the housing unit 150, the movement mechanism 130 is housed in the housing 152 and the detector 140 is housed in the housing 153.

The mounting member 110 and the housing unit 150 are each formed from a light-shielding resin, and the mounting member 110 and the housing unit 150 are black-colored in order to enhance light-shielding properties. A not-illustrated predetermined elastic member is provided between the lower surface of the outer perimeter of the mounting member 110 and the upper surface of the outer perimeter of the housing unit 150. The predetermined elastic member is formed from, for example, light-shielding chloroprene rubber and polyurethane resin, and the predetermined elastic member is black-colored in order to enhance light-shielding properties.

Figure 4A:
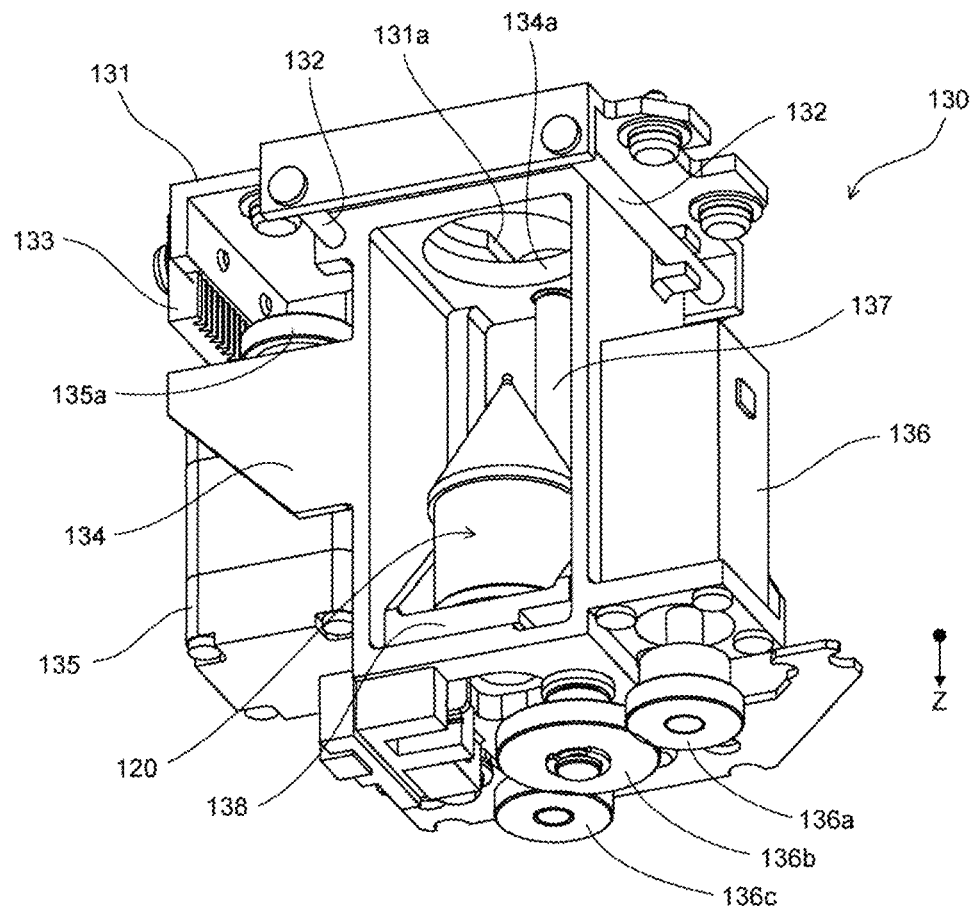
FIG. 4A illustrates the structures of the magnet and the movement mechanism according to Embodiment 1 as viewed from diagonally therebelow.

As shown in FIG. 4A, the movement mechanism 130 includes the member 131, two support shafts 132, a gear portion 133, a supporter 134, a motor 135, a transmission gear 135a, a motor 136, transmission gears 136a to 136c, a screw 137, and a supporter 138. The two support shafts 132 are disposed on the lower surface of the member 131. The gear portion 133 is disposed on the side surface of the member 131 and is flat-plate-shaped. The supporter 134 is supported so as to be movable relative to the two support shafts 132. The two support shafts 132 extend in the radial direction. A hole 134a is formed in the upper surface of the supporter 134. The hole 134a is aligned in position with the hole 131a of the member 131 in the horizontal plane.

The supporter 134 supports the motors 135, 136, the transmission gear 136b, and the screw 137. The motors 135, 136 are implemented as stepping motors. When the drive shaft of the motor 135 is rotated, the transmission gear 135a mounted to the drive shaft is rotated, and driving force is transmitted to the gear portion 133. Thus, the supporter 134 is moved in the radial direction while being supported by the two support shafts 132.

When the drive shaft of the motor 136 is rotated, the transmission gear 136a mounted to the drive shaft is rotated. The transmission gears 136a and 136b mesh with each other, and the transmission gears 136b and 136c mesh with each other. The transmission gear 136b is rotatably mounted to the supporter 134, and the transmission gear 136c is mounted to the screw 137. The screw 137 is rotatably supported by the supporter 134. The supporter 138 is supported by the screw 137 so as to be moved in the up-down direction according to rotation of the screw 137. The magnet 120 is mounted to the supporter 138. Therefore, when the drive shaft of the motor 136 is rotated, driving force is transmitted to the transmission gears 136a, 136b, 136c and the screw 137. Thus, the supporter 138 is moved in the up-down direction.

When the movement mechanism 130 is thus structured, the magnet 120 can be moved in the radial direction according to the motor 135 being driven, and the magnet 120 can be moved in the up-down direction according to the motor 136 being driven. According to the magnet 120 being moved inward in the radial direction, the upper end of the magnet 120 is moved inward in the radial direction of the cartridge 200. According to the magnet 120 being moved outward in the radial direction, the upper end of the magnet 120 is moved outward in the radial direction of the cartridge 200. According to the magnet 120 being moved upward, the upper end of the magnet 120 protrudes upward through the holes 131a, 134a, and is moved close to the cartridge 200. According to the magnet 120 being moved downward, the upper end of the magnet 120 is moved so as to be distant from the cartridge 200.

As the structure for changing a position of the magnet 120 relative to the cartridge 200, a structure other than the above-described structure may be used. For example, in order to move the magnet 120 in the up-down direction, the magnet 120 may be extended and contracted, or the magnet 120 may be rotated about a direction parallel to the horizontal direction.

Figure 4B:
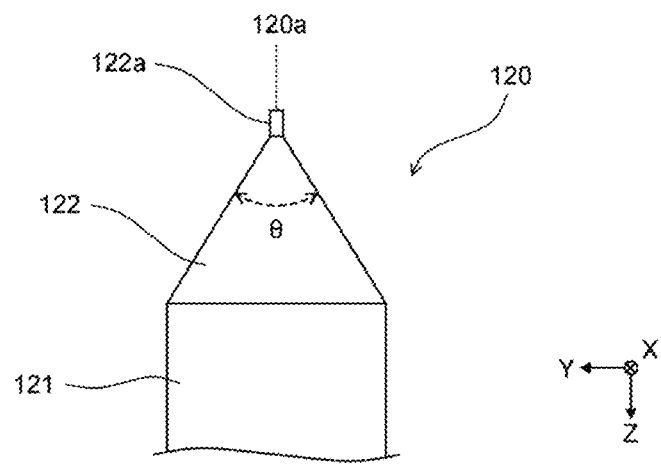
FIG. 4B is a schematic diagram illustrating the structure of the magnet according to Embodiment 1 as viewed from the side thereof.

As shown in FIG. 4B, the magnet 120 includes a permanent magnet 121 and a magnetic body 122. The magnetic body 122 may be either a paramagnetic body or a ferromagnetic body, or may be a combination thereof. The permanent magnet 121 has a cylindrical shape, and the magnetic body 122 has a conic shape. The magnetic body 122 is joined to the upper surface of the permanent magnet 121. At the upper end of the magnetic body 122, a tip portion 122a is formed. The tip portion 122a has a columnar shape having a constant cross-sectional area when cut at the horizontal plane. Specifically, the tip portion 122a has a cylindrical shape. The magnet 120 may have any shape that is tapered such that the closer the cartridge 200 side portion of the magnet 120 is to the cartridge 200, the less the cross-sectional area of the magnet 120 is.

By the magnet 120, a magnetic force is exerted such that the larger the permanent magnet 121 is, in other words, the larger the cross-sectional area of the horizontal surface of the permanent magnet 121 is, the higher the magnetic force exerted onto the magnetic particles in the cartridge 200 is. The less an angle θ of the tapered shape of the magnet 120 is, the more greatly a magnetic force from a central axis 120a of the magnet 120 varies. The less the angle θ is, the higher a force for moving the magnetic particles in the cartridge 200 is. However, in a case where the cross-sectional area of the horizontal surface of the permanent magnet 121 is constant, the less the angle θ is, the longer a distance from the tip portion 122a to the upper surface of the permanent magnet 121 is, so that a magnetic force exerted onto the cartridge 200 by the magnet 120 is reduced. Therefore, in order to increase both a magnetic force exerted onto the magnetic particles and a force for moving the magnetic particles in a well-balanced manner, the angle θ is set as, for example, 60° in Embodiment 1.

In a case where a magnetic force exerted onto the magnetic particles and a force for moving the magnetic particles are high, when the magnetic particles are moved in the cartridge 200 by the magnet 120, the magnetic particles can be prevented from being left behind. Therefore, in a case where the magnet 120 is structured as shown in FIG. 4B, since both a magnetic force exerted onto the magnetic particles and a force for moving the magnetic particles can be increased in a well-balanced manner, the magnetic particles can be prevented from being left behind, and unintended reduction of an amount of light detected by the detector 140 can be inhibited. Therefore, false-negative due to the unintended reduction of an amount of light can be inhibited, thereby allowing highly accurate detection.

The width of the edge of the magnet 120 on the cartridge 200 side, that is, the width of the tip portion 122a is less than at least the minimal width of each region in the channel 220. Thus, a complex collected by the magnet 120 can be smoothly moved in the channel 220 so as not to be caught by the channel 220.

The magnet 120 may be formed only by a permanent magnet. That is, the magnet 120 may be formed as a permanent magnet having a shape obtained by combining the permanent magnet 121 and the magnetic body 122 as described above with each other. However, the magnet 120 that includes the permanent magnet 121 and the magnetic body 122 can be more simply formed with higher accuracy as compared to the magnet 120 having the combined shape.

Figure 5A:
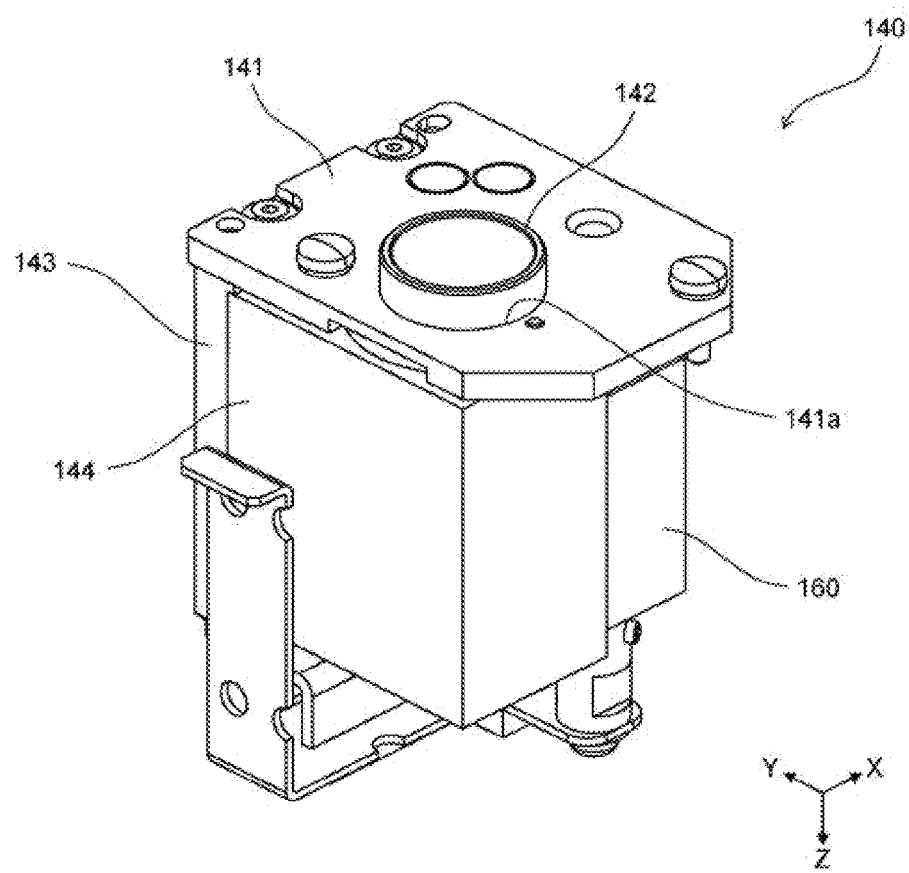
FIG. 5A illustrates the structure of the detector according to Embodiment 1 as viewed from diagonally thereabove.

As shown in FIG. 5A, the detector 140 includes the member 141, the reflector 142, a supporter 143, a light detection unit 144, and a light adjuster 160. The member 141 has a hole 141a that penetrates through the member 141 in the up-down direction. The reflector 142 is disposed so as to be fitted into the hole 141a formed in the member 141. The supporter 143 is disposed on the lower surface of the member 141. The light detection unit 144 and the light adjuster 160 are mounted in the supporter 143.

Figure 5B:
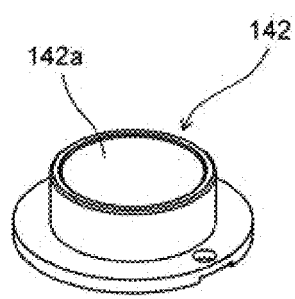
FIG. 5B illustrates a structure of a reflector according to Embodiment 1 as viewed from diagonally thereabove.
Figure 5C:
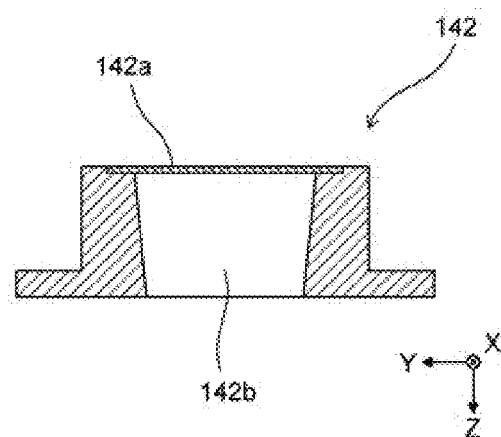
FIG. 5C is a schematic diagram illustrating a cross-section of the reflector according to Embodiment 1 along a YZ plane as viewed from the side thereof.

As shown in FIGS. 5B, 5C, the reflector 142 has a transparent plate 142a in the upper portion thereof. The transparent plate 142a is a member for protecting a light detector 144a described below. The optical effect by the transparent plate 142a can be substantially ignored, and illustration of the transparent plate 142a is omitted for convenience in the following figures. The reflector 142 has, at the center thereof, a hole 142b that penetrates therethrough in the up-down direction. The diameter of the hole 142b in the horizontal plane is reduced downward in the vertical direction. Even if a complex is positioned at any of the center and the end portions in the chamber 216, the reflector 142 allows light generated from the inside of the chamber 216 to be guided to the same degree toward the light detector 144a.

Figure 6A:
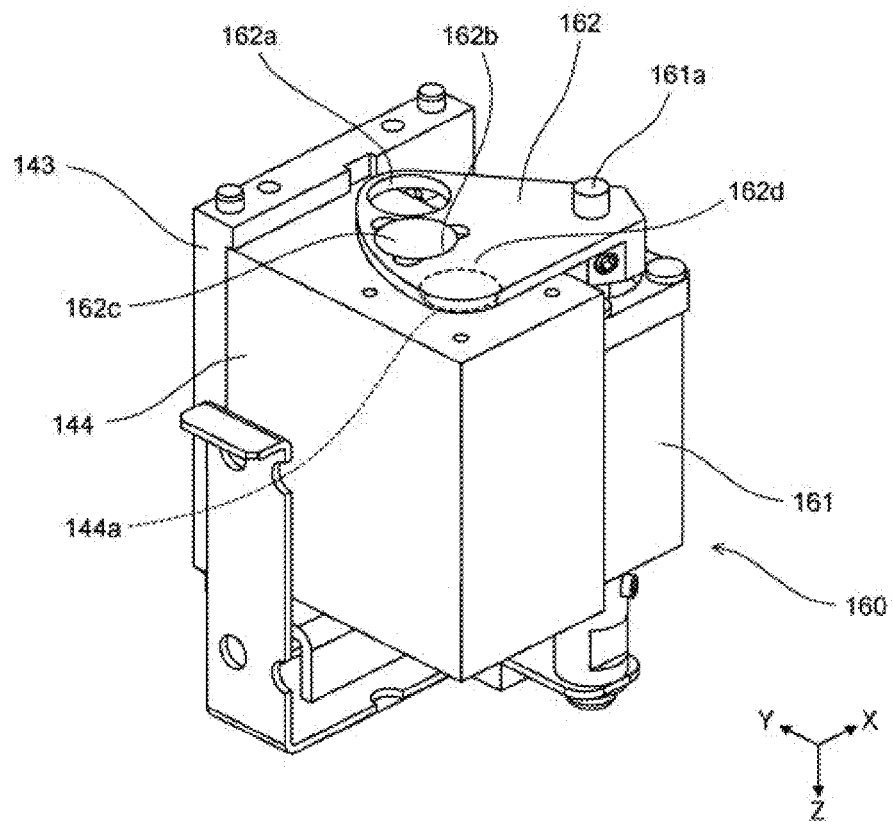
FIG. 6A illustrates the structure of the detector, according to Embodiment 1; which does not have a member and the reflector, as viewed from diagonally thereabove.

FIG. 6A shows a state where the member 141 and the reflector 142 are removed from the detector 140 shown in FIG. 5A.

As shown in FIG. 6A, the light adjuster 160 has a motor 161 and a plate-shaped member 162. The motor 161 is implemented as a stepping motor. The plate-shaped member 162 is mounted to a drive shaft 161a of the motor 161, and includes holes 162a, 162b. The holes 162a, 162b penetrate through the plate-shaped member 162 in the up-down direction. In the hole 162b, a filter member 162c is mounted. The filter member 162c is an ND filter.

When the motor 161 is driven, the plate-shaped member 162 is rotated about the drive shaft 161a. Thus, the hole 162a, the filter member 162c, or a region 162d, other than the holes 162a, 162b, of the plate-shaped member 162 is positioned vertically above the light detector 144a of the light detection unit 144. In a predetermined measurement item, high-intensity light is generated in the chamber 216. In this case, the filter member 162c is positioned vertically above the light detector 144a of the light detection unit 144, and light incident on the light detector 144a is lowered. Thus, saturation of an output signal of the light detector 144a is inhibited.

The light detection unit 144 has the light detector 144a on the upper surface. The light detector 144a has a detection face 144b that opposes the plate-shaped member 162. The light detector 144a optically detects a test substance stored in the chamber 216. The light detector 144a is implemented as, for example, a photomultiplier, a phototube, a photodiode, or the like. When the light detector 144a is implemented as a photomultiplier, a pulse waveform based on reception of photons is outputted from the light detector 144a. The light detection unit 144 has a circuit thereinside, and counts photons at regular intervals on the basis of the output signal from the light detector 144a and outputs a counted value.

Figure 6B:
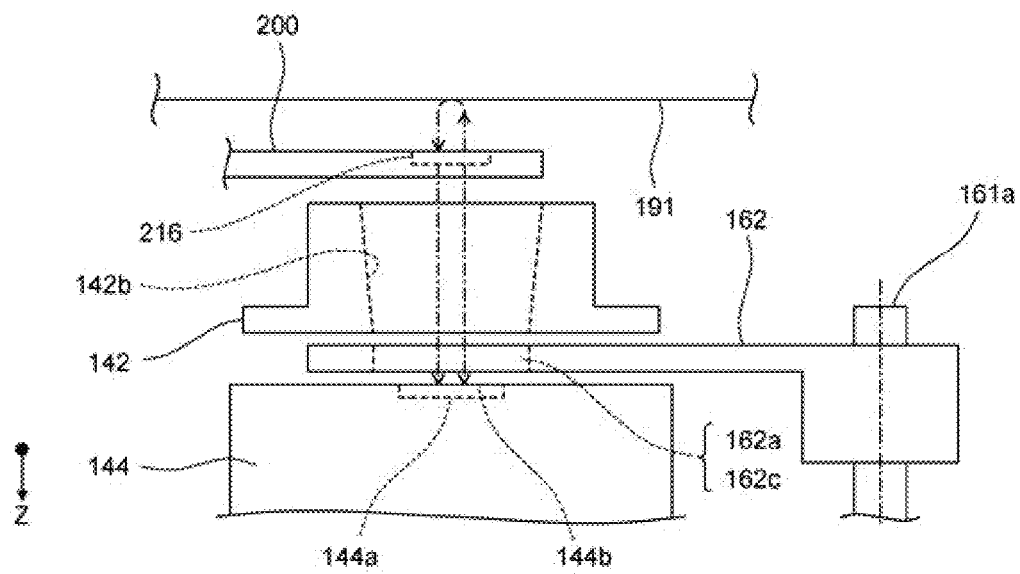
FIG. 6B is a schematic diagram illustrating a state where light generated from a chamber is received by a light detector, according to Embodiment 1, as viewed from the lateral side.

As shown in FIG. 6B, light generated from the chamber 216 of the cartridge 200 spreads upward and downward of the cartridge 200. The light that has spread downward of the cartridge 200 passes through the hole 142b of the reflector 142, passes through the filter member 162c or the hole 162a of the light adjuster 160, and is received by the light detector 144a. The light that has spread upward of the cartridge 200 is reflected by a plate member 191 of the lid portion 102 as described below, and is returned to the chamber 216, and is similarly received by the light detector 144a. A minor may be mounted to the plate member 191 of the lid portion 102, to reflect the light that has spread upward of the cartridge 200.

Figure 7:
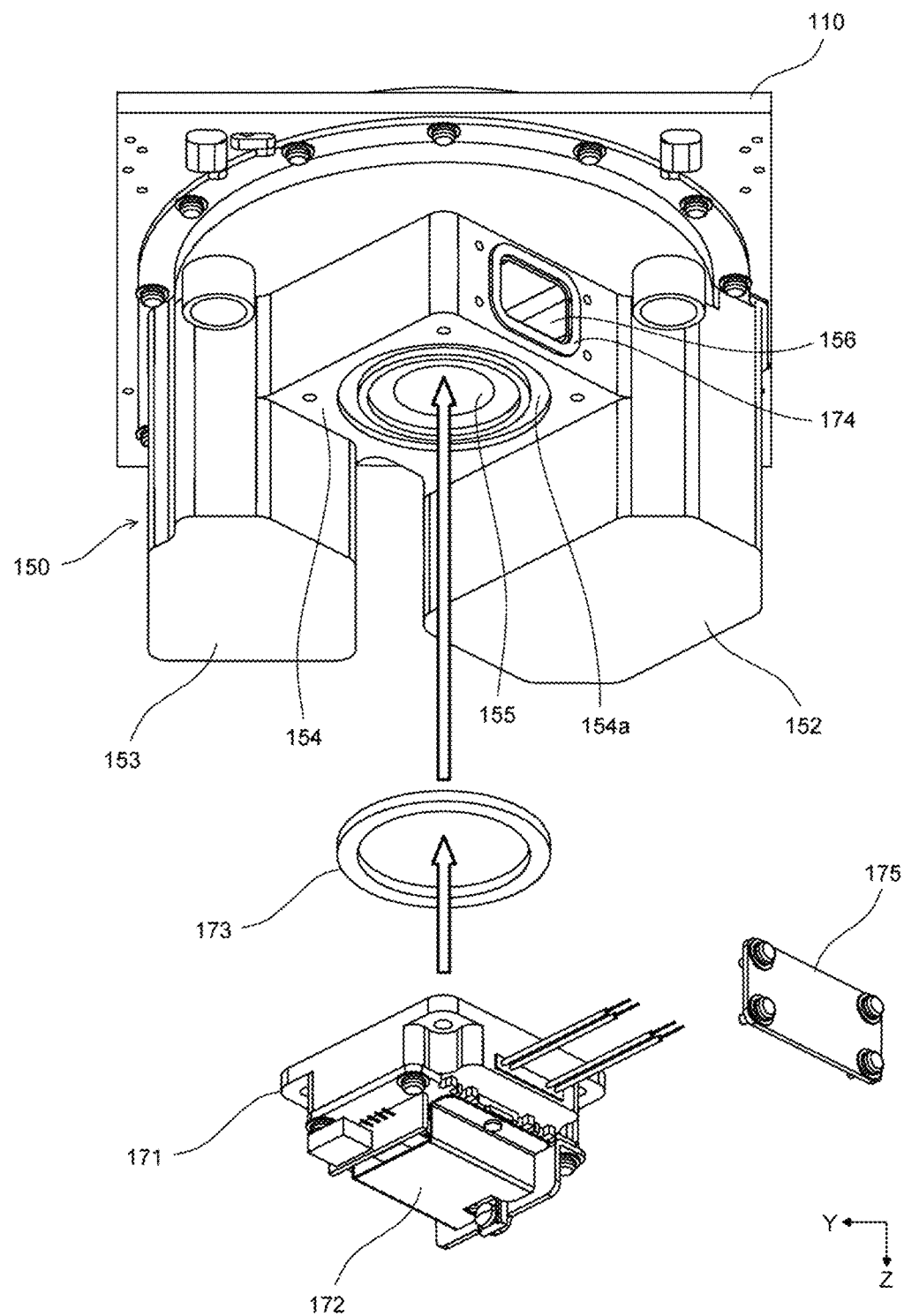
FIG. 7 illustrates a state where a motor, an elastic member, and a lid member are mounted to the housing unit, according to Embodiment 1, as viewed from diagonally therebelow.

As shown in FIG. 7, the outer surface 154 of the housing unit 150 is positioned on the lower side of the housing unit 150, and positioned at the center of the housing unit 150 in the horizontal plane. The outer surface 154 is parallel to the horizontal plane. At the center of the outer surface 154, an outlet of the hole 155 that penetrates through the upper surface 151 to the outer surface 154 in the up-down direction, is formed. The outer surface 154 has a recess 154a around the outlet of the hole 155. The recess 154a has a ring-shaped outer shape as viewed in the vertically upward direction. In the hole 155, a hole 156 is formed so as to be in communication with the outside, from the side of the hole 155.

The motor 171 is implemented as a stepping motor. An encoder 172 is mounted on the lower surface of the motor 171, and detects rotation of a rotation shaft of the motor 171. An elastic member 173 is formed from, for example, a light-shielding polyurethane resin, and the elastic member 173 is black-colored in order to enhance light-shielding properties. The outer shape of the elastic member 173 is ring-shaped such that the elastic member 173 is fitted into the recess 154a of the outer surface 154. The motor 171 is mounted to the outer surface 154 so as to close the hole 155. Specifically, the elastic member 173 is disposed in the recess 154a between the outer surface 154 and the upper surface of the motor 171 that opposes the outer surface 154 such that the elastic member 173 surrounds the hole 155. The motor 171 is mounted on the outer surface 154 so as to press the upper surface of the motor 171 against the elastic member 173. Thus, the lower portion of the hole 155 is closed by the elastic member 173 and the upper surface of the motor 171.

When the motor 171 has been mounted to the outer surface 154, connection and the like of the mechanisms inside the hole 155 are subsequently performed through the hole 156. When the connection and the like of the mechanisms are ended, an elastic member 174 is disposed around the outlet of the hole 156, and the hole 156 is closed by a lid member 175. The elastic member 174 and the lid member 175 are formed so as to have light-shielding properties.

Figure 8:
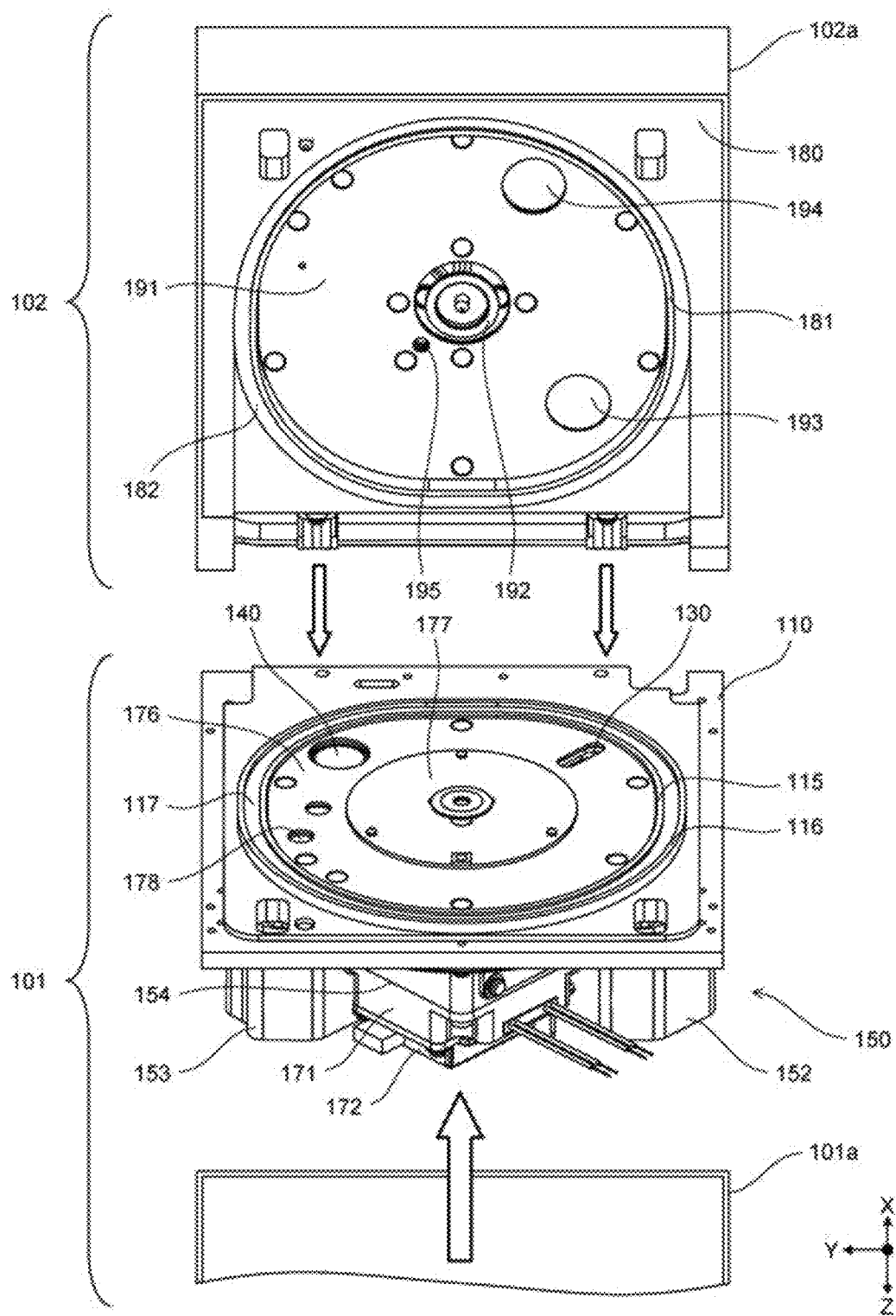
FIG. 8 illustrates a structure of a body portion according to Embodiment 1 as viewed from diagonally thereabove and a structure of a lid portion according to Embodiment 1 as viewed from diagonally therebelow.

As shown in FIG. 8, a plate member 176 and the support member 177 are mounted in a portion, within the protrusion 115, of the mounting member 110. The plate member 176 is formed from a metal having a high thermal conductivity. The heater 321 described below is mounted on the lower surface of the plate member 176. The plate member 176 and the heater 321 have holes at positions corresponding to the holes 111 to 114 of the mounting member 110 shown in FIG. 3. The movement mechanism 130, the detector 140, and the temperature sensor 178 directly oppose the lower surface of the cartridge 200 through these holes as shown in FIG. 8. The temperature sensor 178 is mounted on the lower surface side of the mounting member 110. The temperature sensor 178 detects a temperature of the cartridge 200 by infrared rays.

The support member 177 is mounted at the center of the mounting member 110 through a mounting member 310 described below. The support member 177 is implemented as, for example, a turntable. An elastic member 117 is disposed between the protrusion 115 and the protrusion 116. The elastic member 117 is formed from, for example, a light-shielding polyurethane resin. The elastic member 117 is black-colored in order to enhance light-shielding properties. The elastic member 117 is formed into a closed-loop shape. The upper surface of the elastic member 117 is an elastically deformable joint surface. The mounting member 110 and the housing unit 150 that are thus assembled are mounted in the casing 101a to complete the body portion 101.

FIG. 8 shows the lid portion 102 as viewed from therebelow. The lid portion 102 includes a mounting member 180, the plate member 191, a clamper 192, an imaging portion 193, an illumination portion 194, and the pressing portion 195.

The mounting member 180 is formed from a light-shielding resin, and the mounting member 180 is black-colored in order to enhance light-shielding properties. The plate member 191 and the clamper 192 are disposed in a portion, within a protrusion 181, of the mounting member 180. The plate member 191 is formed from a metal having a high thermal conductivity, similarly to the plate member 176. The heater 322 described below is mounted to the upper surface of the plate member 191. The lower surface of the mounting member 180, the plate member 191, and the heater 322 have holes at positions corresponding to the imaging portion 193, the illumination portion 194, and the pressing portion 195. The imaging portion 193, the illumination portion 194, and the pressing portion 195 directly oppose the upper surface of the cartridge 200 through the holes. The imaging portion 193, the illumination portion 194, and the pressing portion 195 are disposed on the upper surface of the mounting member 180.

The imaging portion 193 takes an image representing a state in the cartridge 200. The imaging portion 193 is implemented as a small camera. The small camera includes, for example, a CCD image sensor, a CMOS image sensor, or the like. The illumination portion 194 illuminates the cartridge 200 when the imaging portion 193 performs image-taking. The illumination portion 194 is implemented as, for example, a light emitting diode. The pressing portion 195 opens the seals 231a, 232a by pressing the seals 231a, 232a. The pressing portion 195 will be described below with reference to FIGS. 10A to 10C.

The clamper 192 is disposed at the center of the mounting member 180. On the lower surface of the mounting member 180, the protrusion 181 that is shaped into a closed-loop is formed. The protrusion 181 protrudes downward along the circumferential direction. On the lower surface of the mounting member 180, a recess is formed outward of the protrusion 181, and an elastic member 182 is disposed in the recess. The elastic member 182 is formed from, for example, a light-shielding polyurethane resin, and the elastic member 182 is black-colored in order to enhance light-shielding properties. The elastic member 182 is shaped into a closed loop. The lower surface of the elastic member 182 is an elastically deformable joint surface.

When assembled, the lid portion 102 is mounted to the body portion 101 so as to be openable and closable relative to the mounting member 110 of the body portion 101. A ventilator 350 described below is mounted in the casing 101a of the body portion 101. The ventilator 350 will be described below with reference to FIGS. 12A, 12B.

Figure 9:
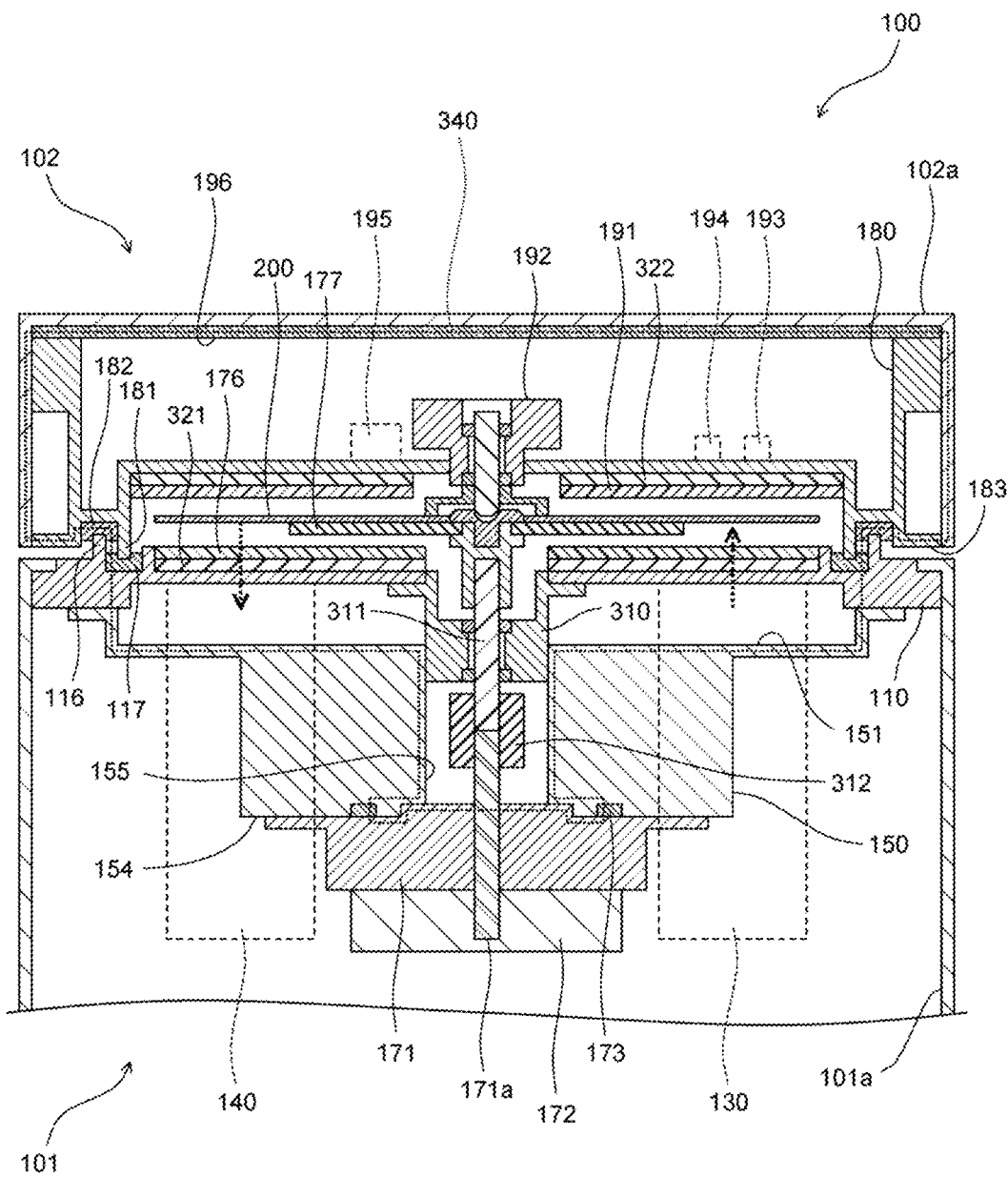
FIG. 9 is a schematic diagram illustrating the cross-section, of the analyzer, which is taken at the plane that is parallel to the YZ plane and that passes through a rotation axis, according to Embodiment 1, as viewed from the side thereof.

FIG. 9 is a schematic diagram illustrating a cross-section of the analyzer 100 taken when cut at a plane that is parallel to the YZ-plane and that passes through the rotation shaft 311. FIG. 9 shows a state where the cartridge 200 is disposed at the analyzer 100 and the lid portion 102 is closed. On the lower surface of the mounting member 110, the movement mechanism 130 that holds the magnet 120, and the detector 140 are mounted as described above. On the upper surface of the mounting member 180, the imaging portion 193, the illumination portion 194, and the pressing portion 195 are mounted as described above. In FIG. 9, positions corresponding to positions at which these components are disposed are indicated by dashed lines.

As shown in FIG. 9, a drive shaft 171a of the motor 171 extends into the hole 155 by the motor 171 being disposed at the outer surface 154. The mounting member 310 is mounted at the upper portion of the hole 155. The mounting member 310 supports the rotation shaft 311 that extends in the up-down direction such that the rotation shaft 311 is rotatable. The rotation shaft 311 is fixed, in the hole 155, to the drive shaft 171a of the motor 171 by the fixing member 312.

The support member 177 for supporting the lower surface of the cartridge 200 is fixed through a predetermined member to the upper portion of the rotation shaft 311. When the motor 171 is driven and the drive shaft 171a is rotated, a rotation driving force is transmitted to the support member 177 through the rotation shaft 311. Thus, the cartridge 200 placed on the support member 177 is rotated about the rotation shaft 311 and the drive shaft 171a. When the cartridge 200 is placed on the support member 177 and the lid portion 102 is closed, the clamper 192 presses the inner circumferential portion of the upper surface of the cartridge 200 such that the cartridge 200 is rotatable.

Figure 13:
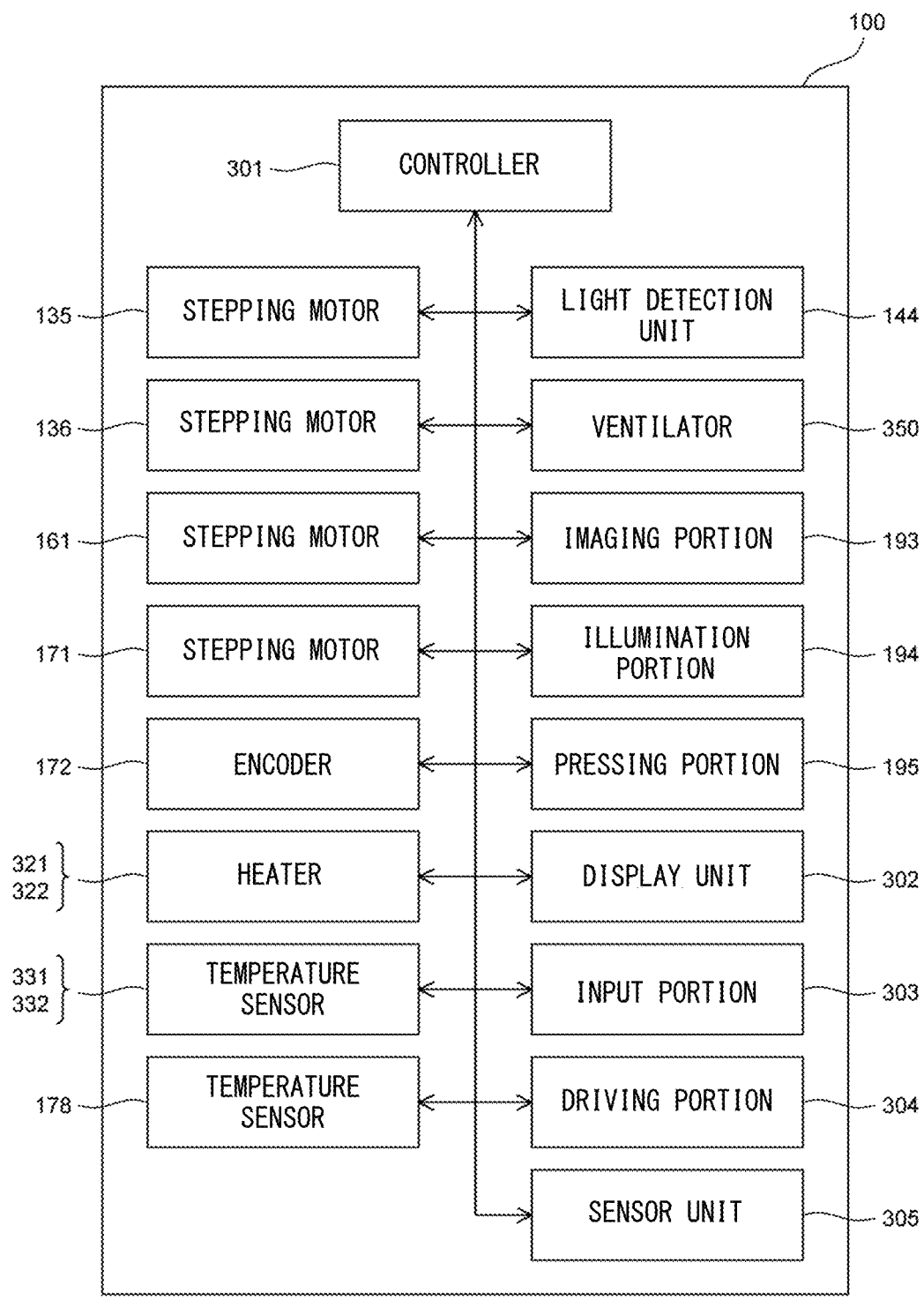
FIG. 13 is a block diagram illustrating a configuration of the analyzer according to Embodiment 1.

The heater 321 is mounted on the lower surface of the plate member 176, and the heater 322 is mounted on the upper surface of the plate member 191. In the heaters 321, 322, a heat generating surface is a plane, and the heat generating surface is disposed so as to be parallel to the cartridge 200. Thus, the cartridge 200 can be efficiently heated. Temperature sensors 331, 332 shown in FIG. 13 are disposed at the plate members 176, 191, respectively. The temperature sensors 331, 332 detect temperatures of the plate members 176, 191, respectively.

The controller 301 described below drives the heaters 321, 322 such that a temperature, of the plate member 176, detected by the temperature sensor 331 in analysis and a temperature, of the plate member 191, detected by the temperature sensor 332 in analysis are predetermined temperatures. The controller 301 drives the heaters 321, 322, on the basis of temperatures detected by the temperature sensors 331, 332, in a control method such as P control, PD control, or PID control. Thus, the temperature of the cartridge 200 is maintained at a predetermined temperature. In Embodiment 1, the predetermined temperature is 42° C. such that reaction in the cartridge 200 appropriately proceeds. Thus, it is particularly important in immunoassay to maintain the temperature of the cartridge 200 so as to be constant. The controller 301 may drive the heaters 321, 322 on the basis of the temperature detected by the temperature sensor 178.

The movement mechanism 130 and the detector 140 act so as to exert a magnetic force onto the cartridge 200 and receive light generated from the cartridge 200 side as indicated by dashed arrows in FIG. 9. On the lower side of the cartridge 200, the mounting member 110 allows light to be easily transmitted in the up-down direction. However, below the mounting member 110, the housing unit 150 is positioned, thereby preventing light from passing between a space below the cartridge 200 and the outside.

Above the mounting member 180 of the lid portion 102, a light-shielding member 196 is disposed between the inner surface of the casing 102a and the mounting member 180. The light-shielding member 196 is formed from a light-shielding resin, and the light-shielding member 196 is black-colored in order to enhance light-shielding properties. A not-illustrated predetermined elastic member is disposed between the lower surface of the outer perimeter of the light-shielding member 196, and the upper surface of the outer perimeter of the mounting member 180. The predetermined elastic member is formed from, for example, light-shielding chloroprene rubber and polyurethane resin, and the predetermined elastic member is black-colored in order to enhance light-shielding properties.

The mounting member 180 has holes at positions where the imaging portion 193, the illumination portion 194, and the pressing portion 195 are disposed. Therefore, at the positions where these components are disposed, light leaks therein in the up-down direction. Accordingly, the mounting member 180 allows light to be transmitted in the up-down direction on the upper side of the cartridge 200. However, the light-shielding member 196 is positioned above the mounting member 180. Thus, light is prevented from passing between a space above the cartridge 200 and the outside.

When the lid portion 102 is closed, the protrusion 116 of the mounting member 110 is pressed against and comes into close contact with the lower surface of the elastic member 182 of the mounting member 180. The protrusion 181 of the mounting member 180 is pressed against and comes into close contact with the upper surface of the elastic member 117 of the mounting member 110. A surface 183 is formed on the lower surface, near the outer perimeter, of the mounting member 180, and a lateral side portion of the inner portion inside the lid portion 102 is covered by the casing 102*a*. Thus, light is prevented from passing between a space lateral to the cartridge 200 and the outside.

Thus, a dark space 340 indicated by dashed lines in FIG. 9 is formed by a light-shielding portion. The light shielding portion on the body portion 101 side is formed by the protrusion 116 of the mounting member 110, the elastic member 117, the outer perimeter portion of the mounting member 110, the housing unit 150, the upper surface of the motor 171, the elastic member 173, the lid member 175, and the elastic member 174. The light shielding portion on the lid portion 102 side is formed by the casing 102*a*, the light-shielding member 196, the surface 183 of the mounting member 180, the protrusion 181 of the mounting member 180, and the elastic member 182. When the lid portion 102 is closed, the light shielding portion on the body portion 101 side and the light shielding portion on the lid portion 102 side are joined to each other in portions lateral to the cartridge 200, and the dark space 340 is surrounded by the light shielding portions. Thus, light is prevented from leaking into the light shielding portion. The structure of the light shielding portion is an exemplary structure, and the components and the like of the light shielding portion are not limited to the above-described ones.

Figure 3:
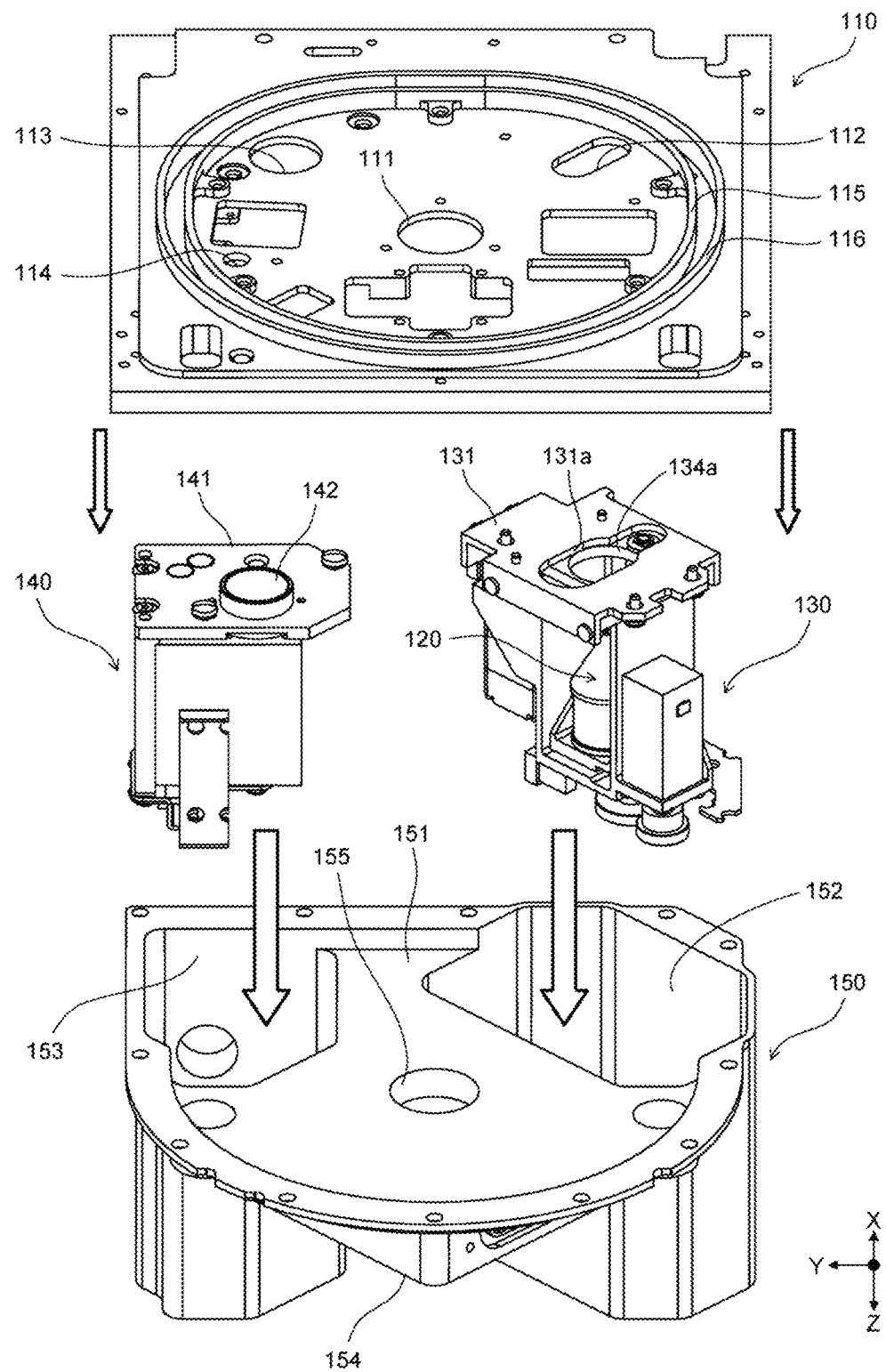
FIG. 3 illustrates structures of a mounting member, a magnet, a movement mechanism, a detector, and a housing unit according to Embodiment 1 as viewed from diagonally thereabove.

As shown in FIG. 3, the upper surface 151 and the housings 152, 153 of the housing unit 150 have holes through which cables pass. The holes may be holes that are opened in the dark space 340. Therefore, the holes through which the cables and the like pass for exchanging signals between the inside of the dark space 340 and the outside of the dark space 340 are all closed by the light-shielding member in order to form the dark space 340. For example, a light-shielding tape, a light-shielding fabric, a heat-shrinkable tube, a grommet, a caulking material, or the like can be used so as to shield gaps between the cables and the holes from light at the outlets of the holes. The light-shielding members are black-colored in order to enhance light-shielding properties.

When the dark space 340 is formed as described above, the support member 177 that supports the cartridge 200, the cartridge 200, and the detection face 144*b* of the light detector 144*a* are disposed in the dark space 340. In Embodiment 1, the magnet 120, the movement mechanism 130, and the detector 140 are disposed in the dark space 340. Thus, even if light generated in reaction in the chamber 216 is extremely low, since light does not enter the dark space 340 from the outside, light generated in the reaction can be accurately detected by the light detector 144*a*. Therefore, accuracy for analyzing a test substance can be enhanced.

As described above, the motor 171 is disposed outside the dark space 340. When the cartridge 200 is rotated, the motor 171 is excited and generates heat. However, when the motor 171 which is a heat source is disposed outside the dark space 340 formed as a closed space as described above, the temperature in the dark space 340 can be inhibited from becoming unstable due to heat from the motor 171. Thus, the temperature of the cartridge 200 can be maintained at a desired temperature. Therefore, a specimen and a reagent in the cartridge 200 can be caused to stably react.

Figure 10A:
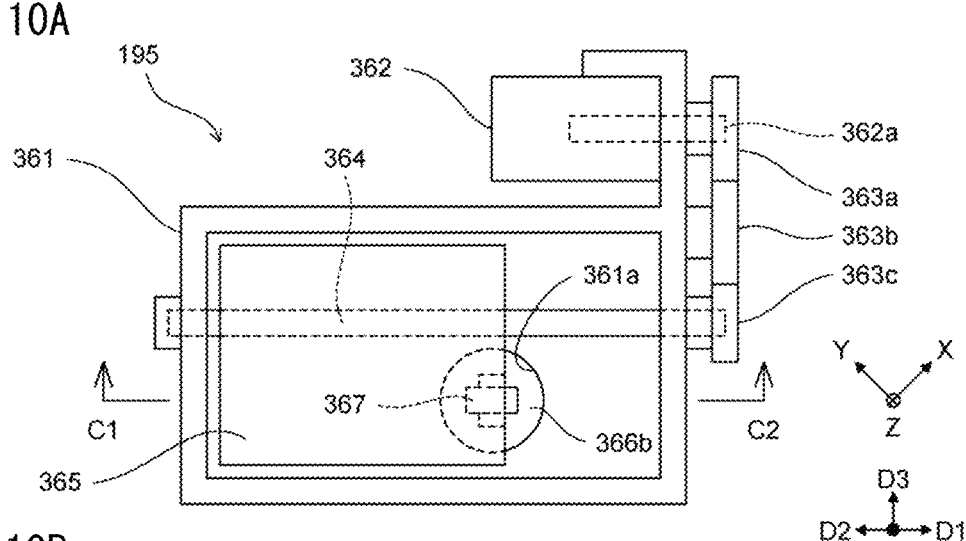
FIG. 10A is a schematic diagram illustrating a structure of a pressing portion according to Embodiment 1 as viewed from thereabove.
Figure 10B:
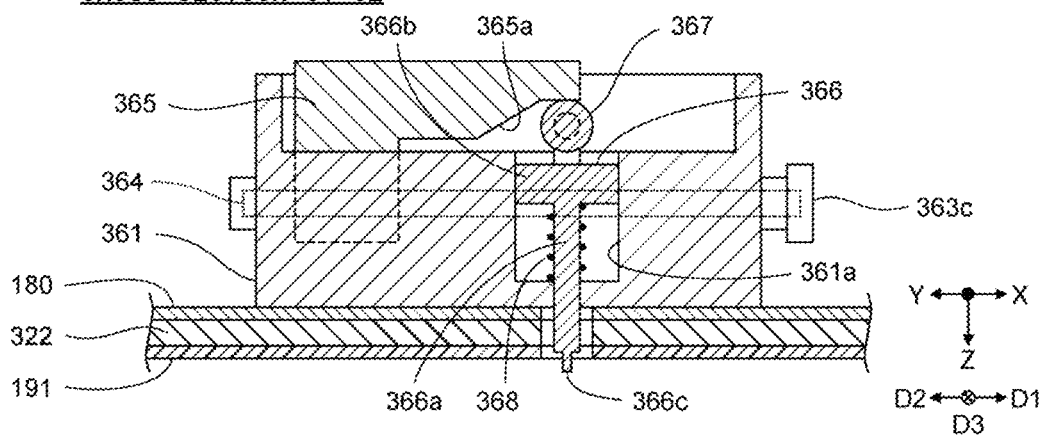
FIG. 10B is a schematic diagram illustrating a cross-section of the structure of the pressing portion according to Embodiment 1 as viewed from the side thereof.
Figure 10C:
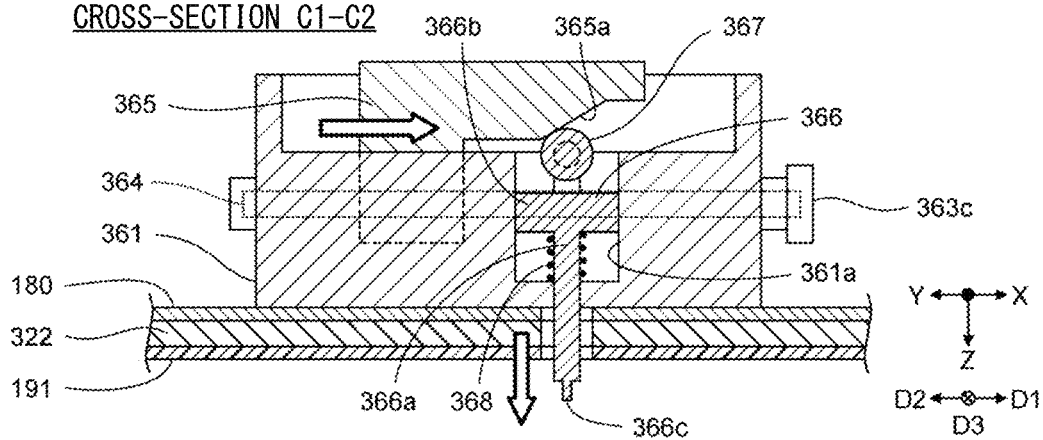
FIG. 10C is a schematic diagram illustrating the cross-section of the structure of the pressing portion according to Embodiment 1 as viewed from the side thereof.

As shown in FIGS. 10A to 10C, the pressing portion 195 includes a mounting member 361, a motor 362, transmission gears 363*a*, 363*b*, 363*c*, a screw 364, a moving member 365, a pin member 366, a roller 367, and a spring 368. In FIGS. 10A to 10C, the D1 direction represents a direction obtained by the X-axis positive direction being rotated clockwise about the Z-axis by 45°. The D2 direction represents a direction obtained by the Y-axis positive direction being rotated counterclockwise about the Z-axis by 45°. The D3 direction represents a direction obtained by the X-axis positive direction being rotated counterclockwise about the Z-axis by 45°. The D3 direction represents a radially outward direction. FIGS. 10B, 10C are each a side view illustrating a cross-section of C1-C2 shown in FIG. 10A, as viewed in the D3 direction.

As shown in FIG. 10B, the mounting member 361 is disposed on the upper surface of the mounting member 180 of the lid portion 102. As shown in FIG. 10A, the motor 362 is mounted to the mounting member 361. The motor 362 is implemented as a stepping motor. The transmission gears 363*a*, 363*b*, 363*c* and the screw 364 are supported by the mounting member 361 so as to be rotatable about the D1-D2 direction. The transmission gears 363*a* and 363*b* mesh with each other, and the transmission gears 363*b* and 363*c* mesh with each other. A drive shaft 362*a* of the motor 362 is connected to the transmission gear 363*a*, and the screw 364 is connected to the transmission gear 363*c*. The moving member 365 is supported by the screw 364 so as to be moved in the D1-D2 direction according to rotation of the screw 364. As shown in FIG. 10B, on the lower surface side of the moving member 365, a cam portion 365*a* is formed as a plane titled relative to the horizontal plane.

As shown in FIGS. 10A, 10B, the mounting member 361 has a hole 361*a* that has a cylindrical shape. As shown in FIG. 10B, the pin member 366 includes a trunk portion 366*a*, a flange portion 366*b* formed at the upper end of the trunk portion 366*a*, and an end portion 366*c* formed at the lower end of the trunk portion 366*a*. The trunk portion 366*a* has a cylindrical shape that extends in the Z-axis direction. The flange portion 366*b* has a cylindrical shape having a diameter that is greater than the trunk portion 366*a*, and that is almost equal to that of the hole 361*a*. The end portion 366*c* has a cylindrical shape having a diameter less than the trunk portion 366*a*. The trunk portion 366*a* passes through a hole formed at the bottom of the hole 361*a*, and through a hole that is formed so as to correspond to the hole formed at the bottom of the hole 361*a* and that penetrates through the mounting member 180, the heater 322, and the plate member 191.

The roller 367 is rotatably disposed at the upper portion of the pin member 366. The roller 367 has a cylindrical shape. The spring 368 is disposed between the lower surface of the flange portion 366*b* and the bottom of the hole 361*a*, and pushes the pin member 366 in the vertically upward direction.

When the pressing portion 195 is thus formed, driving force is transmitted to the transmission gears 363*a*, 363*b*, 363*c*, and the screw 364 according to the motor 362 being driven. Thus, the moving member 365 is moved in the D1-D2 direction. When the moving member 365 is moved in the D1 direction in the state shown in FIG. 10B, the cam portion 365*a* comes into contact with the roller 367 and pushes the roller 367 downward. Thus, as shown in FIG. 10C, the pin member 366 is moved downward. When the moving member 365 is moved in the D2 direction in the state shown in FIG. 10C, the cam portion 365*a* is moved so as to be distant from the roller 367, and the spring 368 pushes the pin member 366 upward. Thus, the position of the pin member 366 is returned to the position shown in FIG. 10B.

When the seal 231*a* is opened, the cartridge 200 is rotated by the support member 177 in a state where the pin member 366 is positioned at the upper side as shown in FIG. 10B, and the seal 231*a* is positioned vertically below the end portion 366*c*. The position vertically below the end portion 366*c* is a position where the pressing portion 195 opens the seal 231a. The motor 362 is driven, and the pin member 366 is moved downward as shown in FIG. 10C. Thus, the seal 231a positioned vertically below the end portion 366c is pressed from thereabove by the end portion 366c, and the seal 231a is opened. Also when the seal 232a is opened, the seal 232a is positioned vertically below the end portion 366c, and the seal 232a is opened by the pressing portion 195, similarly to the seal 231a.

Thus, the seals 231a, 232a are opened by the pressing portion 195 by the seals 231a, 232a being pressed by the end portion 366c. In the opening of the seals 231a and 232a, the seals 231a, 232a are pressed from thereabove by, for example, 10 N force by the end portion 366c. When such a high force is applied to the cartridge 200, displacement, unintended deformation, or the like of the cartridge 200 may occur. Therefore, in order to inhibit the displacement and deformation, as shown in FIG. 11A, the cartridge 200 is supported from therebelow by the support member 177 at the position of the seal 231a.

Figure 11A:
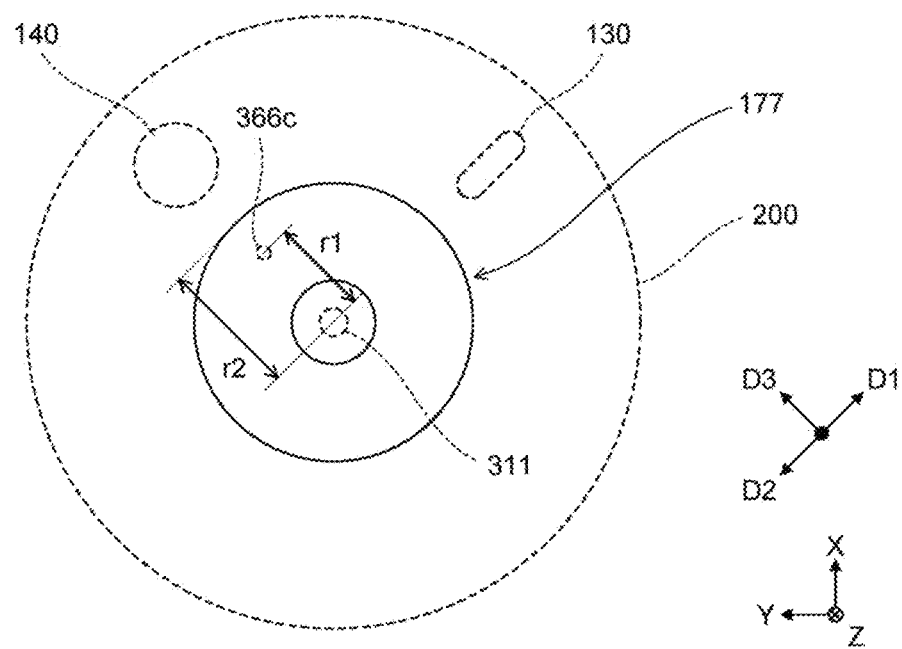
FIG. 11A is a schematic diagram illustrating a structure of a support member according to Embodiment 1 as viewed from thereabove.

FIG. 11A illustrates the support member 177 as viewed from thereabove. In FIG. 11A, the cartridge 200 which is placed on the support member 177 is indicated by dashed lines for convenience. The movement mechanism 130 and the detector 140 portions that directly oppose the lower surface of the cartridge 200 through holes formed in the plate member 176 shown in FIG. 8, are indicated by dashed lines for convenience. The rotation shaft 311, and the end portion 366c of the pin member 366 are indicated by dashed lines for convenience.

As shown in FIG. 11A, r1 represents a distance from the rotation shaft 311 to the end portion 366c in the horizontal plane. In other words, r1 represents a distance from the rotation shaft 311 to a position at which the cartridge 200 is pressed by the pressing portion 195. The support member 177 is disposed at a position opposing the pressing portion 195 across the cartridge 200. Specifically, the support member 177 is a turntable that has a radius r2 that is greater than at least the distance r1, and disposed in a portion from the rotation shaft 311 side to the position opposing the pressing portion 195.

Thus, in opening of the seals 231a, 232a, also when the pressing portion 195 presses the seals 231a, 232a, and a pressing force is applied to the cartridge 200, the cartridge 200 is supported by the support member 177 that acts as a base. Therefore, in the opening of the seals 231a, 232a, displacement or damage may not occur in the cartridge 200, and the cartridge 200 is appropriately supported at a predetermined position. Therefore, measurement accuracy is inhibited from being reduced by the opening.

As shown in FIG. 11A, the radius r2 of the support member 177 is set such that the support member 177 does not overlap the movement mechanism 130 and the detector 140 portions that directly oppose the lower surface of the cartridge 200 as viewed from thereabove. Thus, the magnet 120 can access the cartridge 200 in a state where the cartridge 200 is placed on the support member 177. Therefore, the magnetic particles collected by the magnet 120 in one chamber can be smoothly transferred to another chamber. Light from the cartridge 200 is not blocked by the support member 177, so that detection by the detector 140 can be appropriately performed.

When the radius r2 of the support member 177 is set as a great value in such a range that the support member 177 does not overlap the movement mechanism 130 and the detector 140 portions that oppose the lower surface of the cartridge 200, the cartridge 200 can be more stably supported. However, if the radius r2 of the support member 177 is increased, a load on the motor 171 that rotates the support member 177 is increased. In this case, if the rotation time of the motor 171 is increased, or a rotation speed is frequently changed, the motor 171 may be out of order or heat generation of the motor 171 may be increased. Therefore, the radius r2 of the support member 177 is preferably minimized in such a range as to cover positions at which pressing force from the pressing portion 195 is received by the support member 177.

Even if the radius r2 of the support member 177 is thus set so as to be as small a value as possible, an area and a weight of the support member 177 are increased as compared to a case where the support member simply supports the cartridge 200. In this case, the motor 171 that drives the support member 177 is increased in size, and the heat generation of the motor 171 is increased. However, as described above, the motor 171 is disposed outside the dark space 340. Therefore, even if heat generation of the motor 171 is increased, a temperature in the dark space 340 can be inhibited from becoming unstable, and the measurement can appropriately proceed.

Figure 11B:
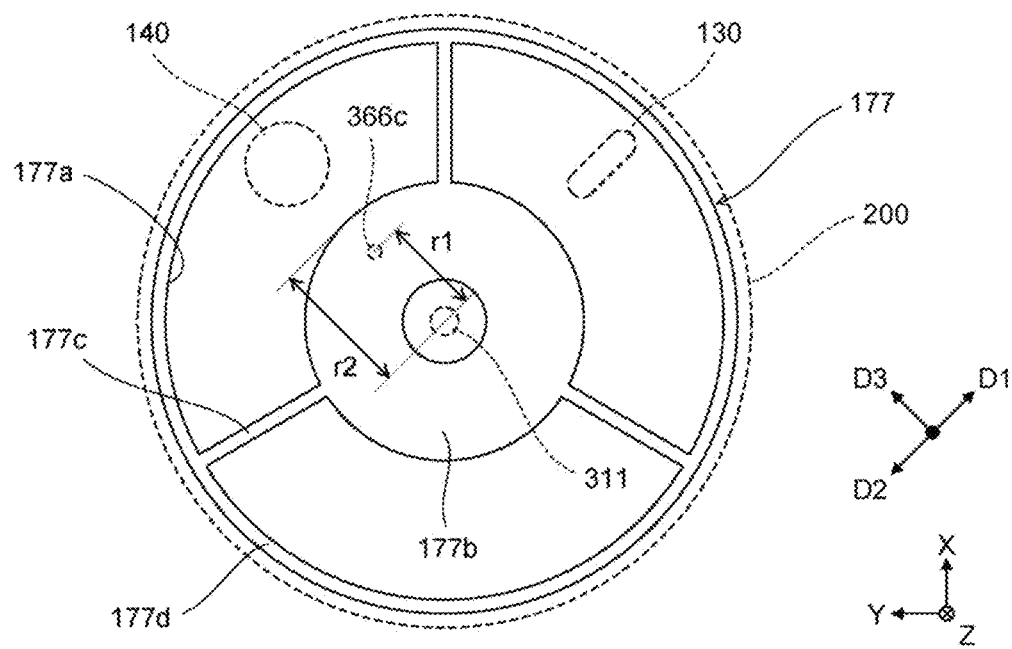
FIG. 11B is a schematic diagram illustrating a structure of a support member according to modification of Embodiment 1 as viewed from thereabove.

As shown in FIG. 11B, the radius for the outermost circumferential portion of the support member 177 may be set to be almost equal to the radius of the cartridge 200. In this case, for example, the support member 177 has three holes 177a that penetrate through the support member 177 in the Z-axis direction. An inner circumferential portion 177b having the radius r2 is formed inward of the three holes 177a, similarly to the case shown in FIG. 11A. A connecting portion 177c is disposed between the two holes 177a adjacent to each other so as to extend in the radial direction. An outer circumferential portion 177d positioned at the outermost circumference of the support member 177 is supported by the three connecting portions 177c.

The size of the hole 177a is set such that the movement mechanism 130 and the detector 140 portions that are open upward directly oppose the lower surface of the cartridge 200 through each hole 177a. The size of the hole 177a is set such that the chambers 211 to 216 and the channel 220 do not overlap the support member 177 when the cartridge 200 is placed on the support member 177.

When the support member 177 is formed as shown in FIG. 11B, the lower surface, of the cartridge 200, positioned below the seals 231a, 232a can be supported by the inner circumferential portion 177b, as in the case shown in FIG. 11A. In the case shown in FIG. 11B, a portion, of the cartridge 200, near the outer circumference is supported by the outer circumferential portion 177d, whereby the cartridge 200 can be more stably supported as compared to the case shown in FIG. 11A.

In a case where the cartridge 200 is placed at a predetermined position on the support member 177, the shape of the support member 177 shown in FIG. 11A, and the shapes of the inner circumferential portion 177b and the outer circumferential portion 177d shown in FIG. 11B may not necessarily be round.

Figure 12A:
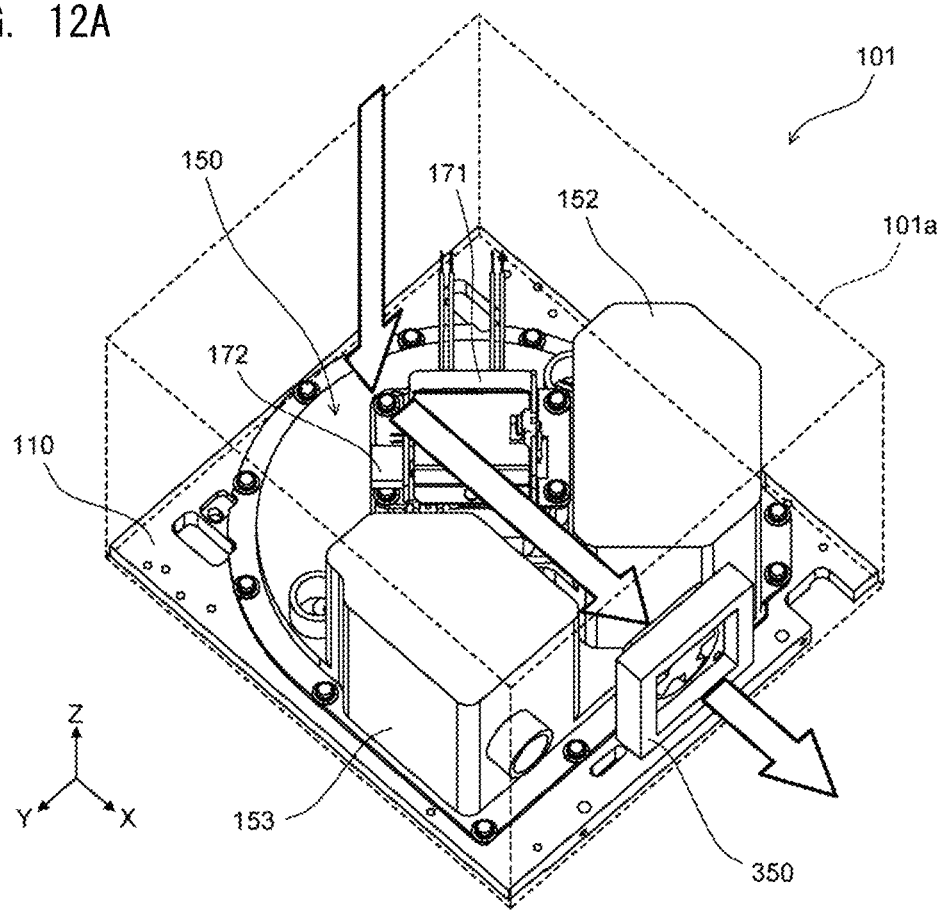
FIG. 12A illustrates an internal structure of the body portion according to Embodiment 1 as viewed from therebelow.
Figure 12B:
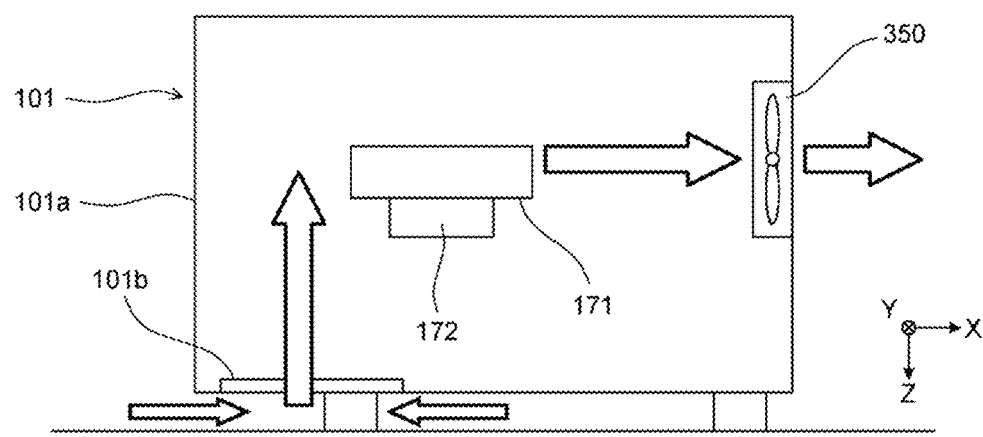
FIG. 12B is a schematic diagram illustrating the internal structure of the body portion according to Embodiment 1 as viewed from the side thereof.

As shown in FIGS. 12A, 12B, the ventilator 350 is mounted on the rear surface of the casing 101a of the body portion 101. The ventilator 350 is implemented as a fan. The ventilator 350 dissipates, to the outside of the analyzer 100, heat generated by the motor 171 mounted in the outer surface 154 of the housing unit 150. The bottom surface of the casing 101a of the body portion 101 is distant from a setting surface by means of a leg portion over a predetermined distance. A ventilation opening 101b is formed in the bottom surface at the front portion of the casing 101a. By the ventilator 350 being driven, air taken in through the ventilation opening 101b passes through the motor 171, and is discharged backward from the analyzer 100 as indicated by an outline arrow. Air taken in from the outside at a position of the ventilator 350 may pass through the motor 171, and may be discharged through the ventilation opening 101*b* in the direction opposite to the direction indicated by the outline arrow.

In the planar view, that is, as viewed in the vertical direction, the outline of the body portion 101 is rectangular, and the outline of the motor 171 is also rectangular. The motor 171 is disposed in the body portion 101 such that the corner of the motor 171 and the corner of the body portion 101 are misaligned in the planar view. In the planar view, the detector 140 that includes the light detector 144*a* is disposed in a space between the motor 171 and the corner of the body portion 101. Similarly, in the planar view, the magnet 120 and the movement mechanism 130 are disposed in a space between the motor 171 and another corner of the body portion 101. Thus, the shape of the body portion 101 in the planar view can be made compact, thereby reducing the size of the analyzer 100.

In the housing unit 150, the housings 152, 153 are formed for housing members disposed in the dark space 340. The housings 152, 153 are each shaped such that the outer side surface on the motor 171 side projects. The motor 171 is disposed lateral to the housing 152 so as to be spaced from the housing 152, and is disposed lateral to the housing 153 so as to be spaced from the housing 153. That is, the motor 171 is disposed in the outer surface 154. The motor 171 is thus disposed lateral to the housings 152, 153, whereby the analyzer 100 can be prevented from being increased in size in the height direction. The space is formed between the housing 152 and the motor 171, and the space is formed between the housing 153 and the motor 171. Therefore, the spaces allow convection of air to occur as shown in FIGS. 12A, 12B. Therefore, heat of the motor 171 can be effectively removed.

The housings 152, 153 are formed in the housing unit 150 so as to be spaced from each other. The motor 171 is disposed between the housing 152 and the housing 153. The ventilator 350 is disposed so as to oppose the space between the housings 152 and 153. Thus, air easily passes around the motor 171 through the space for the housings 152 and 153, whereby heat of the motor 171 can be effectively removed.

The ventilator 350 is disposed at a position as high as the motor 171 so as to oppose the motor 171. Thus, air around the motor 171 is easily guided to the outside of the analyzer 100, whereby heat generated in the motor 171 can be efficiently exhausted. As described above, the motor 171 is disposed outside the dark space 340, and the ventilator 350 is also disposed outside the dark space 340. Thus, increase of the temperature in the dark space 340 can be effectively inhibited without interfering with light-shielding properties of the light shielding portion that forms the dark space 340.

In Embodiment 1, the controller 301 described below drives, when receiving an instruction for starting analysis, the heaters 321, 322 to increase the temperature of the cartridge 200. At this time, the controller 301 controls the operation of the ventilator 350 on the basis of the temperature, of the cartridge 200, detected by the temperature sensor 178. For example, when the temperature of the cartridge 200 is lower than 40° C., the controller 301 causes the ventilator 350 to halt, and, when the temperature of the cartridge 200 is higher than 40° C., the controller 301 drives the ventilator 350. Thus, as compared to a case where the ventilator 350 is driven immediately after an instruction for starting analysis is received, a time period before the temperature of the cartridge 200 converges to 42° C., can be shortened, and power consumption of the ventilator 350 and the heaters 321, 322 can be reduced.

As shown in FIG. 13, the analyzer 100 includes the motors 135, 136, 161, 171, the encoder 172, the heaters 321, 322, the temperature sensors 331, 332, 178, the light detection unit 144, the ventilator 350, the imaging portion 193, the illumination portion 194, and the pressing portion 195, as described above. The analyzer 100 also includes the controller 301, a display unit 302, an input portion 303, a driving portion 304, and a sensor unit 305.

The controller 301 includes, for example, a processing unit and a storage unit. The processing unit includes, for example, a CPU, an MPU, and the like. The storage unit is implemented as, for example, a flash memory, a hard disk, or the like. The controller 301 receives signals from the components, respectively, of the analyzer 100, and controls the components of the analyzer 100. The display unit 302 and the input portion 303 are provided in, for example, a side surface portion of the body portion 101 or an upper surface portion of the lid portion 102. The display unit 302 is implemented as, for example, a liquid crystal panel. The input portion 303 is implemented as, for example, a button or a touch panel. The driving portion 304 includes another mechanism disposed in the analyzer 100. The sensor unit 305 includes a sensor for detecting a predetermined portion of the rotating cartridge 200, a sensor for detecting a mechanism moved to the position of an origination point by the motors 135, 136, 161, and another sensor disposed in the analyzer 100.

Figure 14:
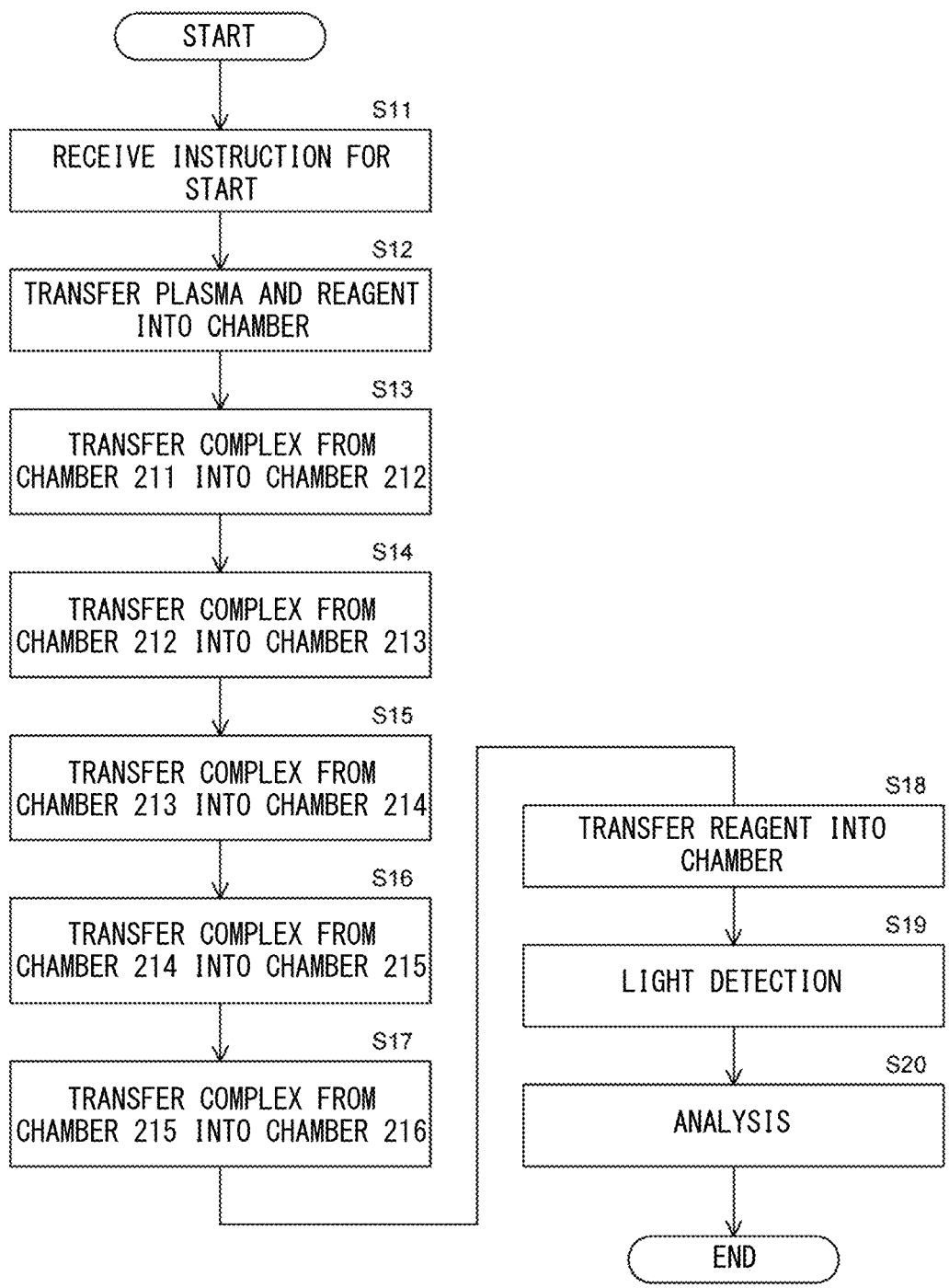
FIG. 14 is a flow chart showing an operation of the analyzer according to Embodiment 1.

Next, an operation of the analyzer 100 will be described with reference to FIG. 14.

Firstly, an operator injects, through the opening 241, a blood specimen collected from a subject, and places the cartridge 200 on the support member 177. A test substance in the blood specimen includes, for example, an antigen. An example of the antigen is Hepatitis B surface antigen (HBsAg). The test substance may be one or more of an antigen, an antibody, and protein.

Predetermined reagents are stored in advance in the liquid storage portions 231, 232 and the chamber 211 of the cartridge 200. Specifically, an R1 reagent is stored in the liquid storage portion 231 positioned for the chamber 211 in the radial direction. An R2 reagent is stored in the chamber 211. An R3 reagent is stored in the liquid storage portion 231 positioned for the chamber 212 in the radial direction. Washing liquid is stored in the liquid storage portion 231 positioned for each of the chambers 213 to 215 in the radial direction. An R4 reagent is stored in the liquid storage portion 231 positioned for the chamber 216 in the radial direction. An R5 reagent is stored in the liquid storage portion 232.

In the following control, the controller 301 obtains a rotational position of the drive shaft 171*a* of the motor 171 on the basis of an output signal from the encoder 172 connected to the motor 171. The controller 301 causes a sensor to detect a predetermined portion of the rotating cartridge 200, to obtain a position of the cartridge 200 in the circumferential direction. Alternatively, the cartridge 200 may be placed at a predetermined position on the support member 177. Thus, the controller 301 allows each component of the cartridge 200 to be positioned at a predetermined position in the circumferential direction.

The controller 301 obtains positions of the mechanisms moved by the motors 135, 136, 161 on the basis of an output signal from the sensor for detecting the mechanism moved to the position of the originating point by the motors 135, 136, 161. Thus, the controller 301 allows the mechanisms moved by the motors 135, 136, 161, that is, the magnet 120 and the plate-shaped member 162 to be each positioned at a predetermined position.

In step S11, the controller 301 receives, through the input portion 303, an instruction for start from an operator, and starts step S12 and the following process steps.

In step S12, the controller 301 transfers plasma and the reagents into the chambers. Specifically, the controller 301 drives the motor 171 to rotate the cartridge 200, and drives the pressing portion 195 to press down the six seals 231a positioned at positions opposing the pressing portion 195. The controller 301 drives the motor 171 to rotate the cartridge 200, and transfers the plasma positioned in the region 243b, into the chamber 211, by a centrifugal force, and transfers, into the chambers 211 to 216, the reagents stored in the six liquid storage portions 231. Thus, the plasma, the R1 reagent, and the R2 reagent are mixed in the chamber 211. The R3 reagent is transferred into the chamber 212, the washing liquid is transferred into each of the chambers 213 to 215, and the R4 reagent is transferred into the chamber 216.

After the plasma and the reagents have been transferred in step S12, the controller 301 performs agitation. Specifically, the controller 301 drives the motor 171 so as to change between two different rotation speeds at predetermined time intervals while causing the motor 171 to rotate in a predetermined direction. For example, the controller 301 performs agitation by changing an electric current applied to the motor 171 at predetermined time intervals, or by switching the driving of the motor 171 between on and off at predetermined time intervals. Thus, an Euler force generated in the circumferential direction is varied at predetermined time intervals, whereby liquid in each of the chambers 211 to 216 is agitated. This agitation is performed not only in step S12 but also in steps S13 to S18 similarly after transfer.

The controller 301 may perform agitation by changing a rotating direction of the motor 171 at predetermined time intervals. However, when the motor 171 is driven in this manner, load on the motor 171 is increased. Therefore, as described above, the motor 171 is preferably driven so as to change between two rotation speeds while the motor 171 is caused to rotate in a predetermined direction.

The R1 reagent includes a capture substance that binds to the test substance. The capture substance includes, for example, an antibody that binds to the test substance. The antibody is, for example, a biotin-bound HBs monoclonal antibody. The R2 reagent includes magnetic particles in a liquid component. The magnetic particles are, for example, streptavidin-bound magnetic particles the surfaces of which are coated with avidin. In step S12, the plasma, the R1 reagent, and the R2 reagent are mixed and agitated, whereby the test substance and the R1 reagent bind to each other by antigen-antibody reaction. By reaction between antigen-antibody reaction product and the magnetic particles, the test substance bound to the capture substance in the R1 reagent binds to the magnetic particles by means of the capture substance. Thus, a complex in which the test substance and the magnetic particles bind to each other, is generated.

Next, in step S13, the controller 301 causes the complex in the chamber 211 to be transferred from the chamber 211 into the chamber 212. Thus, the complex generated in the chamber 211 and the R3 reagent are mixed with each other in the chamber 212. The R3 reagent includes a labelling substance. The labelling substance includes a label, and a capture substance that specifically binds to the test substance. For example, the labelling substance is a labelled antibody which includes an antibody used as the capture substance. In step S13, the complex generated in the chamber 211 and the R3 reagent are mixed and agitated, so that the complex generated in the chamber 211 and the labelled antibody contained in the R3 reagent react with each other. Thus, a complex in which the test substance, the capture antibody, the magnetic particles, and the labelled antibody are bound, is generated.

Figure 15:
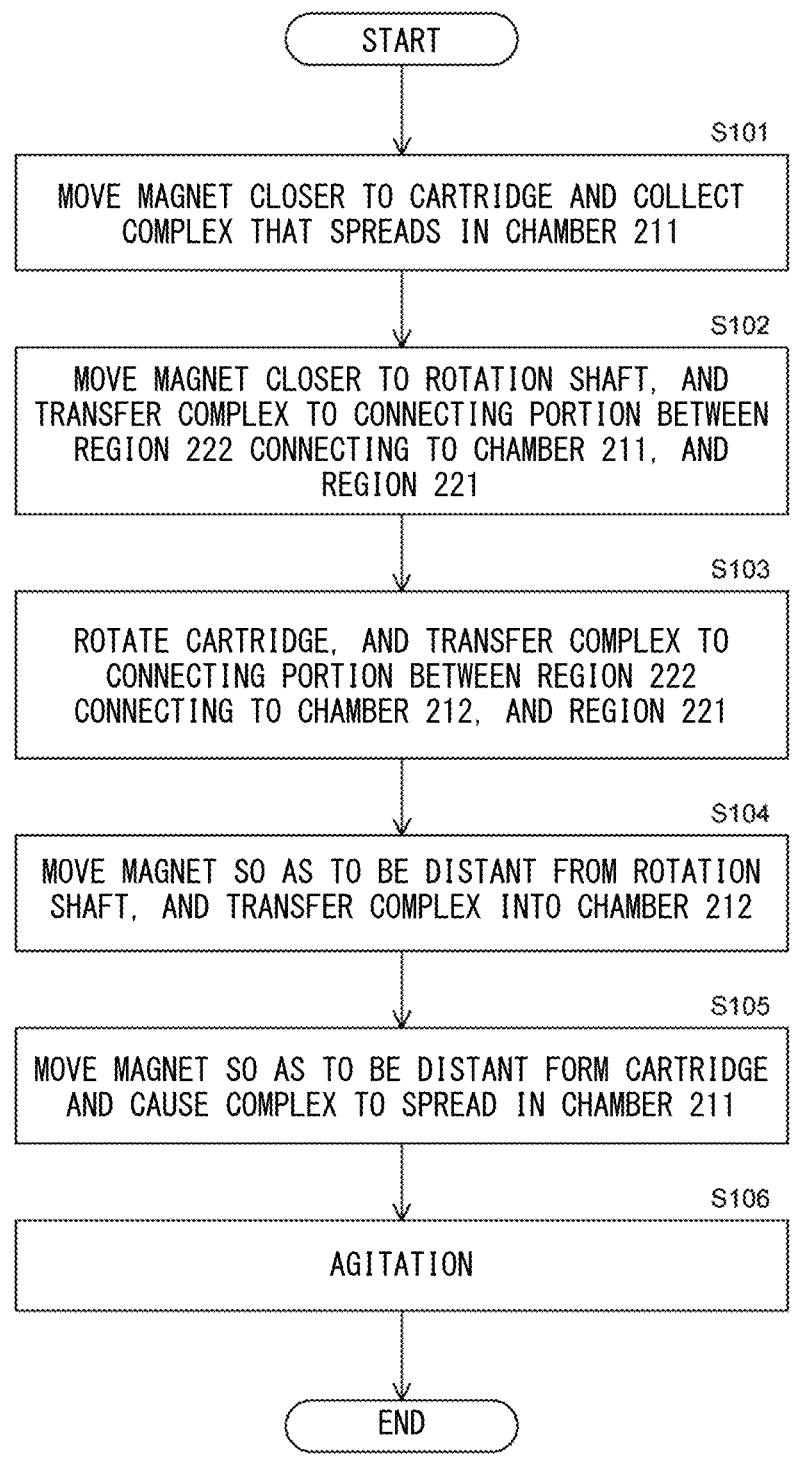
FIG. 15 is a flow chart showing an operation of the analyzer in the case of a complex being transferred between chambers adjacent to each other, according to Embodiment 1.

The process step of step S13 will be described in detail with reference to FIG. 15. FIG. 15 is a flow chart showing step S13 in FIG. 14 in detail. In the following description, FIG. 15 is mainly referred to, and FIG. 16A to FIG. 17C showing state transitions are referred to as appropriate.

Figure 16A:
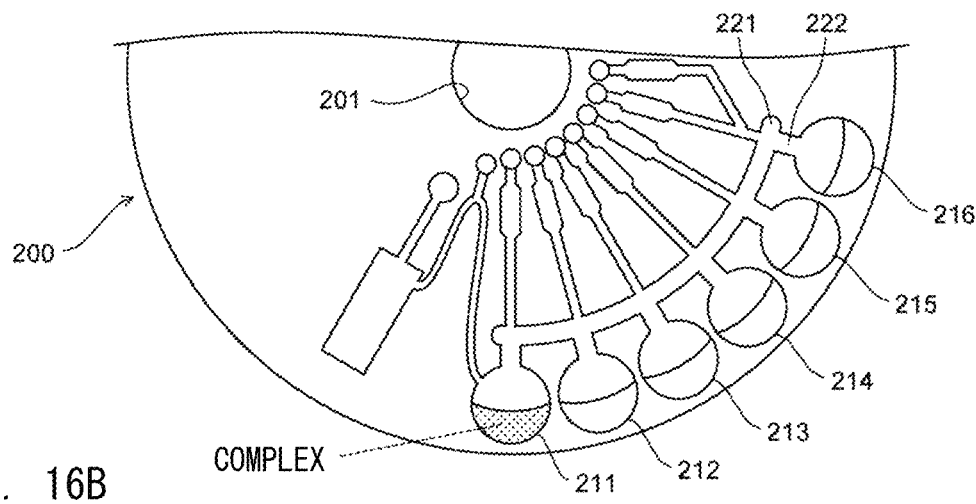
FIG. 16A schematically illustrates a state transition in which a complex is transferred between chambers adjacent to each other, according to Embodiment 1.
Figure 16B:
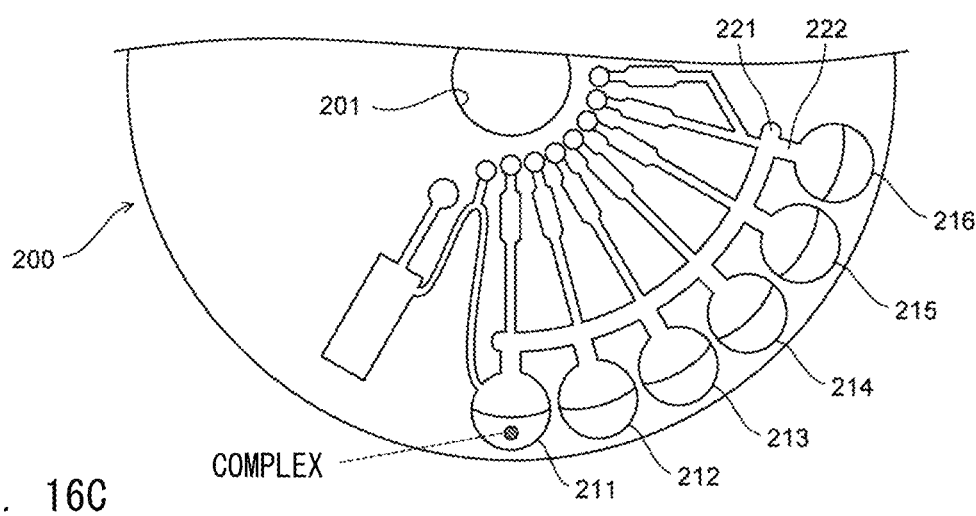
FIG. 16B schematically illustrates a state transition in which the complex is transferred between the chambers adjacent to each other, according to Embodiment 1.

When the process step of step S12 has ended, the complex spreads in the chamber 211 as shown in FIG. 16A. In step S101, the controller 301 drives the movement mechanism 130 to cause the magnet 120 to move close to the cartridge 200, thereby collecting the complex that spreads in the chamber 211, as shown in FIG. 16B. At this time, in the horizontal plane, the controller 301 causes the tip portion 122a of the magnet 120 to move close to a region that is at the center, in the circumferential direction, of the chamber 211, and that is close to the outer side, in the radial direction, of the chamber 211.

In Embodiment 1, an amount of mixture, in the chamber 211, which contains the complex is less than the total capacity of the chamber 211. If the amount of the mixture stored in the chamber 211 is less than the total capacity of the chamber 211, it is assumed that an amount of mixture varies among regions in the chamber 211. However, in a case where the test substance, the R1 reagent, and the R2 reagent are mixed in the chamber 211, and a centrifugal force is thereafter applied to the chamber 211 in the agitation, as described above, the mixture is unevenly distributed in an outer side portion in the chamber 211 at any time. Accordingly, in a case where the complex in the chamber 211 is collected by the magnet 120, when the tip portion 122a of the magnet 120 is positioned in a storage region of the mixture that is unevenly distributed in the chamber 211, that is, positioned in a region closer to the outer side of the chamber 211, the complex in the mixture in the chamber 211 can be assuredly collected at the position of the magnet 120.

An amount of the mixture, in each of the chambers 212 to 215, which contains the complex is also less than the total capacity of the corresponding chamber of the chambers 212 to 215. Therefore, similarly to the case for the chamber 211, when the magnet 120 is positioned in the region closer to the outer side, the complex in the mixture in each of the chambers 212 to 215 can be assuredly collected at the position of the magnet 120.

Figure 16C:
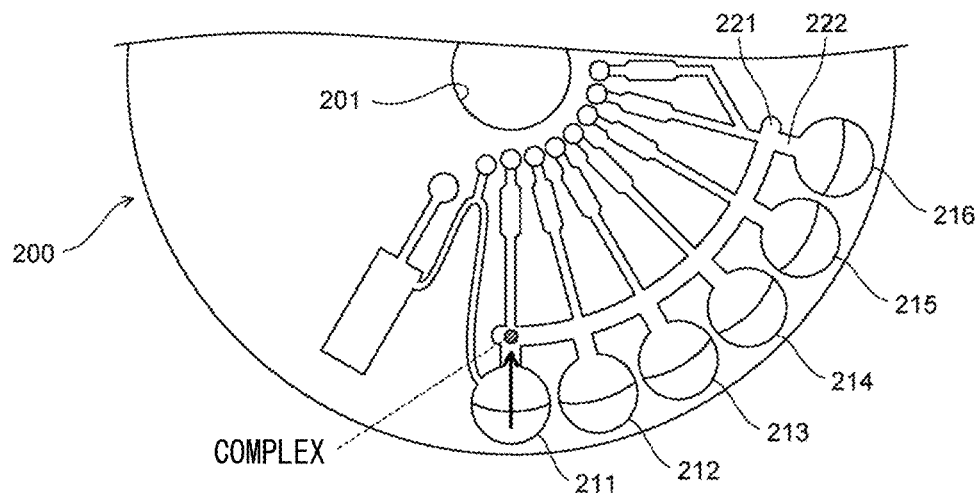
FIG. 16C schematically illustrates a state transition in which the complex is transferred between the chambers adjacent to each other, according to Embodiment 1.

In step S102, the controller 301 drives the movement mechanism 130 to move the magnet 120 so as to be closer to the rotation shaft 311, and causes the complex to be transferred to the connecting portion between the region 222 that connects to the chamber 211, and the region 221, as shown in FIG. 16C. In step S102, the speed at which the complex is moved relative to the cartridge 200 is preferably lower than or equal to 10 mm/second so as to prevent the complex from being left in the chamber 211. Specifically, for example, the speed is 0.5 mm/second. The magnet 120 is moved by the movement mechanism 130 such that the speed at which the complex is moved can be as described above.

Figure 17A:
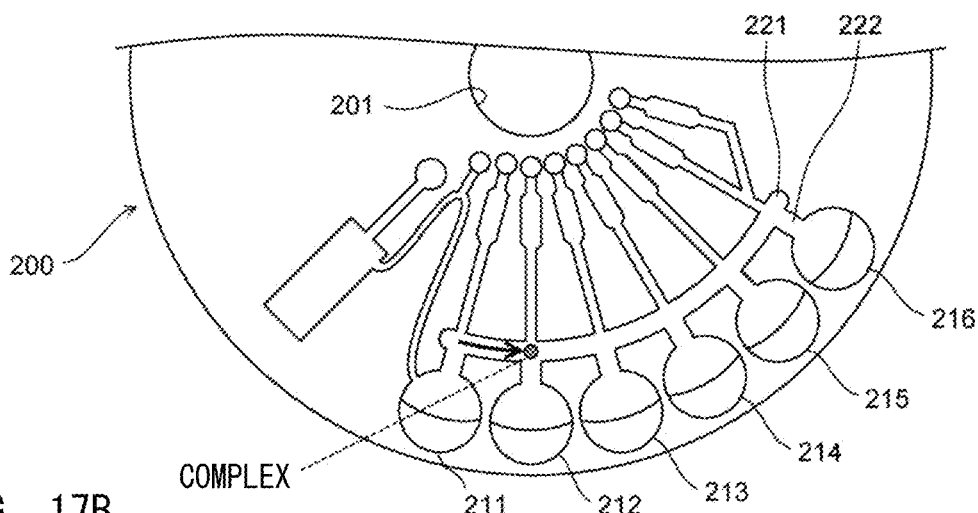
FIG. 17A schematically illustrates a state transition in which the complex is transferred between the chambers adjacent to each other, according to Embodiment 1.

In step S103, the controller 301 drives the motor 171 to rotate the cartridge 200, and causes the complex to be transferred to the connecting portion between the region 221, and the region 222 that connects to the chamber 212, as shown in FIG. 17A. In step S103, the speed at which the complex is moved relative to the cartridge 200 is also set similarly as in step S102. The cartridge 200 is rotated by the motor 171 such that the speed at which the complex is moved can be as described above.

Figure 17B:
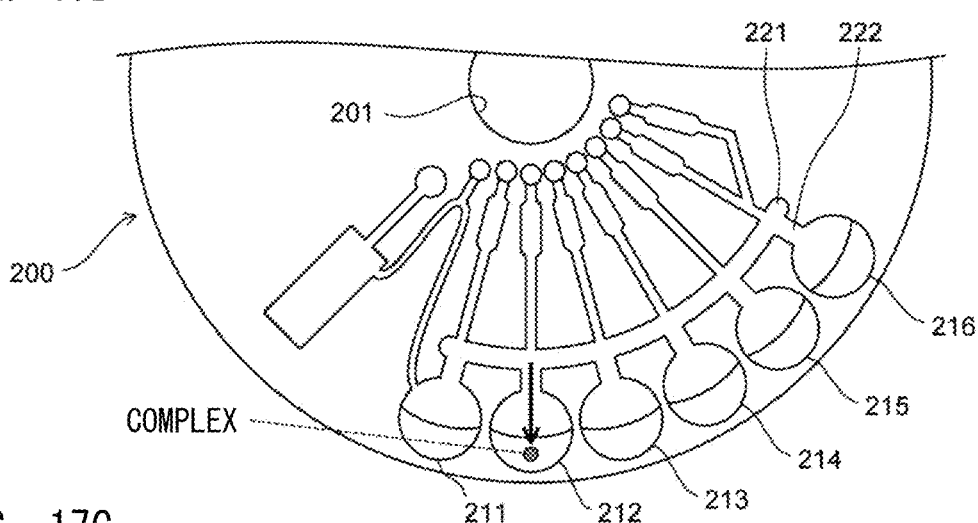
FIG. 17B schematically illustrates a state transition in which the complex is transferred between the chambers adjacent to each other, according to Embodiment 1.
Figure 17C:
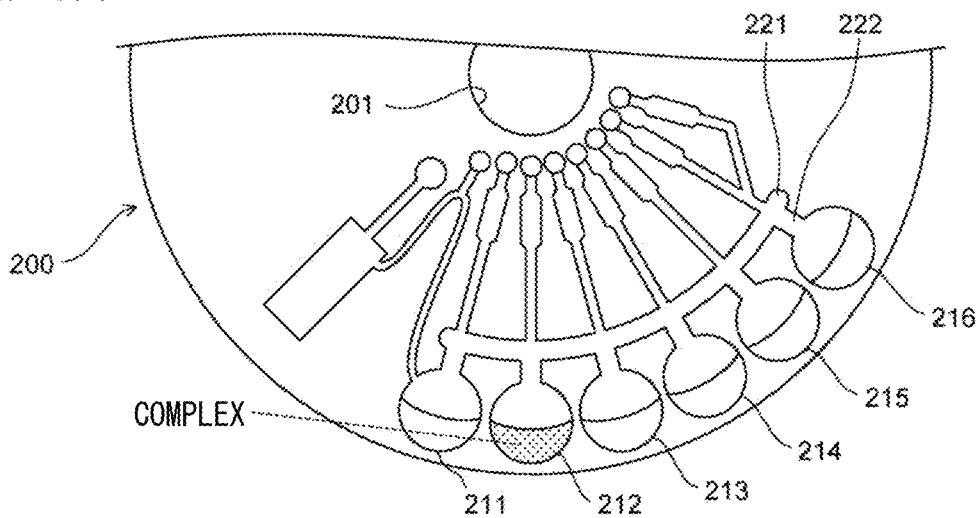
FIG. 17C schematically illustrates a state transition in which the complex is transferred between the chambers adjacent to each other, according to Embodiment 1.

In step S104, the controller 301 drives the movement mechanism 130 to move the magnet 120 so as to be distant from the rotation shaft 311, and causes the complex to be transferred into the chamber 212, as shown in FIG. 17B. In step S104, the speed at which the complex is moved relative to the cartridge 200 is set similarly as in step S102. In step S105, the controller 301 drives the movement mechanism 130 to move the magnet 120 so as to be distant from the cartridge 200, and causes the complex to spread in the chamber 212, as shown in FIG. 17C.

As described above, in steps S101 to S105, the controller 301 causes the magnet 120 to move close to the cartridge 200 at a position opposing the chamber 211, and thereafter causes the magnet 120 to move along the channel 220 while the magnet 120 is maintained close to the cartridge 200, and causes the magnet 120 to be positioned at a position opposing the chamber 212. Thereafter, the controller 301 causes the magnet 120 to move so as to be distant from the cartridge 200, and cancels magnetic collection of the complex by the magnet 120. Thus, the complex can be assuredly prevented from being left in the chamber 211 and the channel 220.

In step S106, the controller 301 performs control so as to perform the above-described agitation. At this time, the magnetic collection of the complex is cancelled before the agitation, and the complex spreads in the chamber 212, thereby assuredly agitating the liquid in the chamber 212.

As described above, the process step of step S13 in FIG. 14 is performed. The transfer and agitation shown in steps S101 to S106 are performed similarly also in steps S14 to S17 described below.

Returning to FIG. 14, in step S14, the controller 301 causes the complex in the chamber 212 to be transferred from the chamber 212 into the chamber 213. Thus, in the chamber 213, the complex generated in the chamber 212 and washing liquid are mixed. In step S14, by the complex generated in the chamber 212 and washing liquid being mixed and agitated, the complex and unreacted substances are separated from each other in the chamber 213. That is, in the chamber 213, the unreacted substances are removed by washing.

In step S15, the controller 301 causes the complex in the chamber 213 to be transferred from the chamber 213 into the chamber 214. Thus, in the chamber 214, the complex generated in the chamber 212 and washing liquid are mixed. Also in the chamber 214, unreacted substances are removed by washing.

In step S16, the controller 301 causes the complex in the chamber 214 to be transferred from the chamber 214 into the chamber 215. Thus, in the chamber 215, the complex generated in the chamber 212 and washing liquid are mixed. Also in the chamber 215, unreacted substances are removed by washing.

In step S17, the controller 301 causes the complex in the chamber 215 to be transferred from the chamber 215 into the chamber 216. Thus, in the chamber 216, the complex generated in the chamber 212 and the R4 reagent are mixed. The R4 reagent is a reagent for dispersing the complex generated in the chamber 212. The R4 reagent is, for example, a buffer. In step S17, the complex generated in the chamber 212 and the R4 reagent are mixed and agitated, whereby the complex generated in the chamber 212 is dispersed.

In step S18, the controller 301 causes the R5 reagent to be transferred into the chamber 216. Specifically, the controller 301 drives the motor 171 to rotate the cartridge 200, and drives the pressing portion 195 to press down the seal 232a positioned at a position opposing the pressing portion 195. The controller 301 drives the motor 171 to rotate the cartridge 200, and causes the R5 reagent stored in the liquid storage portion 232 to be transferred into the chamber 216 by a centrifugal force. Thus, in the chamber 216, the R5 reagent is further mixed with the mixture generated in step S17.

The R5 reagent is a luminescent reagent containing a luminescent substrate that generates light by reaction with the labelled antibody bound to the complex. In step S18, the mixture generated in step S17 and the R5 reagent are mixed and agitated, to prepare a sample. The sample causes chemiluminescence by reaction between the luminescent substrate and the labelling substance bound to the complex.

In step S19, the controller 301 drives the motor 171 to position the chamber 216 vertically above the light detector 144a, and causes the light detector 144a to detect light generated from the chamber 216. In step S20, the controller 301 performs immune analysis on the basis of the light detected by the light detector 144a. When the light detector 144a is implemented as a photomultiplier, a pulse waveform based on reception of photons is outputted by the light detector 144a. The light detection unit 144 counts the photons at regular intervals on the basis of the output signal from the light detector 144a and outputs the counted value. The controller 301 performs analysis for presence or absence of the test substance and an amount of the test substance on the basis of the counted value outputted by the light detection unit 144, and causes the display unit 302 to display the result of the analysis.

As described above, the complex is transferred sequentially into the chambers 211 to 216. In a case where the complex is transferred through the plurality of the chambers, the complex is likely to be left in the chambers 211 to 215 and the channel 220. However, in a case where the complex is assuredly transferred by using the magnet 120 as described above, the complex can be assuredly prevented from being left therein. Thus, unintended reduction of an amount of light detected by the light detector 144a can be inhibited. Therefore, false-negative due to the unintended reduction of an amount of light can be inhibited, thereby allowing highly accurate detection.

The chemiluminescence is light generated by using energy caused by chemical reaction. For example, the chemiluminescence is light that is emitted when molecules excited by chemical reaction into an excited state are returned from the exited state to a ground state. For example, the chemiluminescence can be generated by reaction between an enzyme and a substrate, can be generated by application of electrochemical stimuli to a labelling substance, can be generated in an LOCI (luminescent oxygen channeling immunoassay), or can be generated according to bioluminescence. In Embodiment 1, any chemiluminescence may be performed.

The complex may be formed by a test substance being bound to a substance which is excited to generate fluorescence when light having a predetermined wavelength is applied. In this case, a light source for applying light to the chamber 216 is disposed. The light detector 144a detects fluorescence which is generated by the substance that binds to the complex being excited by the light from the light source.

The magnetic particles may be any particles that contain a magnetic material as a base and are used for standard immunoassay. For example, the magnetic particles containing, as the base, $Fe_2O_3$ and/or $Fe_3O_4$, cobalt, nickel, ferrite, magnetite, or the like, can be used. The magnetic particles may be coated with a binding substance for binding to a test substance, or may bind to a test substance by means of a capture substance for binding the magnetic particles and the test substance to each other. The capture substance is an antigen, an antibody, or the like that binds the magnetic particles and the test substance mutually to each other.

The labelling substance contains, for example, a label for chemiluminescence and a capture substance that specifically binds to a test substance. The capture substance is not particularly limited, and may be any substance that specifically binds to a test substance. In Embodiment 1, the capture substance binds to a test substance by antigen-antibody reaction. More specifically, in Embodiment 1, the capture substance is an antibody. When the test substance is an antibody, the capture substance may be an antigen of the antibody. When the test substance is a nucleic acid, the capture substance may be a nucleic acid that is complementary to the test substance. Examples of the label contained in the labelling substance include an enzyme, a fluorescent substance, a radioisotope, and the like. Examples of the enzyme include alkaline phosphatase (ALP), peroxidase, glucose oxidase, tyrosinase, acid phosphatase, and the like. When chemiluminescence is electrochemiluminescence, the label is not particularly limited, and may be any substance that emits light by electrochemical stimuli. Examples of the label include a ruthenium complex. Examples of the fluorescent substance include fluorescein isothiocyanate (FITC), green fluorescent protein (GFP), luciferin, and the like. Examples of the radioisotope include 125I, 14C, 32P, and the like.

When the label is an enzyme, a luminescent substrate for the enzyme may be appropriately selected from known luminescent substrates according to the enzyme to be used. When the enzyme is alkaline phosphatase, examples of the luminescent substrate include: chemiluminescent substrates such as CDP-Star (registered-trademark), (disodium 4-chloro-3-(methoxyspiro[1,2-dioxetane-3,2'-(5'-chloro)tricyclo[3.3.1.13,7]decane]-4-yl)phenylphosphate), and CSPD (registered-trademark) (disodium 3-(4-methoxyspiro[1,2-dioxetane-3,2-(5'-chloro)tricyclo[3.3.1.13,7]decane]-4-yl) phenylphosphate); luminescent substrates such as p-nitrophenyl phosphate, 5-bromo-4-chloro-3-indolyl phosphate (BCIP), 4-nitro blue tetrazolium chloride (NBT), and iodonitrotetrazolium (INT); fluorescent substrates such as 4-methylumbelliferyl phosphate (4MUP); and chromogenic substrates such as 5-bromo-4-chloro-3-indolyl phosphate (BLIP), disodium 5-bromo-6-chloro-indolyl phosphate, and p-nitrophenyl phosphate; and the like.

Next, the inventors made an experiment for verification example 1 where, when a complex was moved, the magnet 120 was used in all the movement operations as described above, and made an experiment for verification example 2 where, when a complex was moved, the magnet 120 was not used in a part of the movement operations.

In verification example 1, similarly to Embodiment 1, the controller 301 caused the magnet 120 to move close to the cartridge 200 to collect a complex by the magnet 120, caused the complex to be moved into the chambers 211 to 216 by moving the magnet 120, and caused the light detector 144a to detect light generated from the chamber 216. In verification example 2, after the controller 301 caused a complex to be positioned in a connecting portion between the region 222 connecting to the chamber 212 and the region 221, the controller 301 caused the magnet 120 to be moved such that the magnet 120 was distant from the cartridge 200, and caused the complex to be transferred into the chamber 212 by a centrifugal force generated by the motor 171 being driven. In verification example 2, the transfer procedure in which the complex was transferred from the chamber 211 to the connecting portion and the transfer procedure in which the complex was transferred from the chamber 212 to the chamber 216 were exactly the same as those in verification example 1. Also in verification example 2, the controller 301 caused the light detector 144a to detect light generated from the chamber 216.

The inventors obtained a counted value based on detection by the light detector 144a in each of verification examples 1 and 2. In verification examples 1 and 2, the measurement was performed by using "HISCL TSH C1" that was a calibrator manufactured by SYSMEX CORPORATION. That is, the calibrator replaced the plasma in the above-described analysis in Embodiment 1, and was transferred into the chamber 211, and the obtained complex was transferred and luminescence was detected.

Figure 18A:
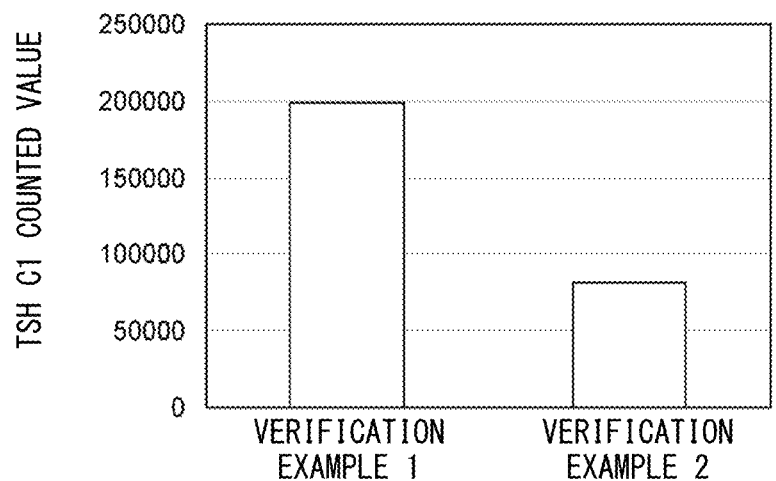
FIG. 18A shows a graph indicating counted values obtained by experiments according to verification examples 1, 2 of Embodiment 1.

As shown in FIG. 18A, the counted value was about 200000 in verification example 1, while the counted value was about 80000 and was a low value in verification example 2. Since the procedures were different between verification examples 1 and 2, it is considered that the complex was left in the path and the counted value was greatly reduced in verification example 2 since the magnet 120 was not used in a part of the movement operations when the complex was moved in verification example 2.

Figure 18B:
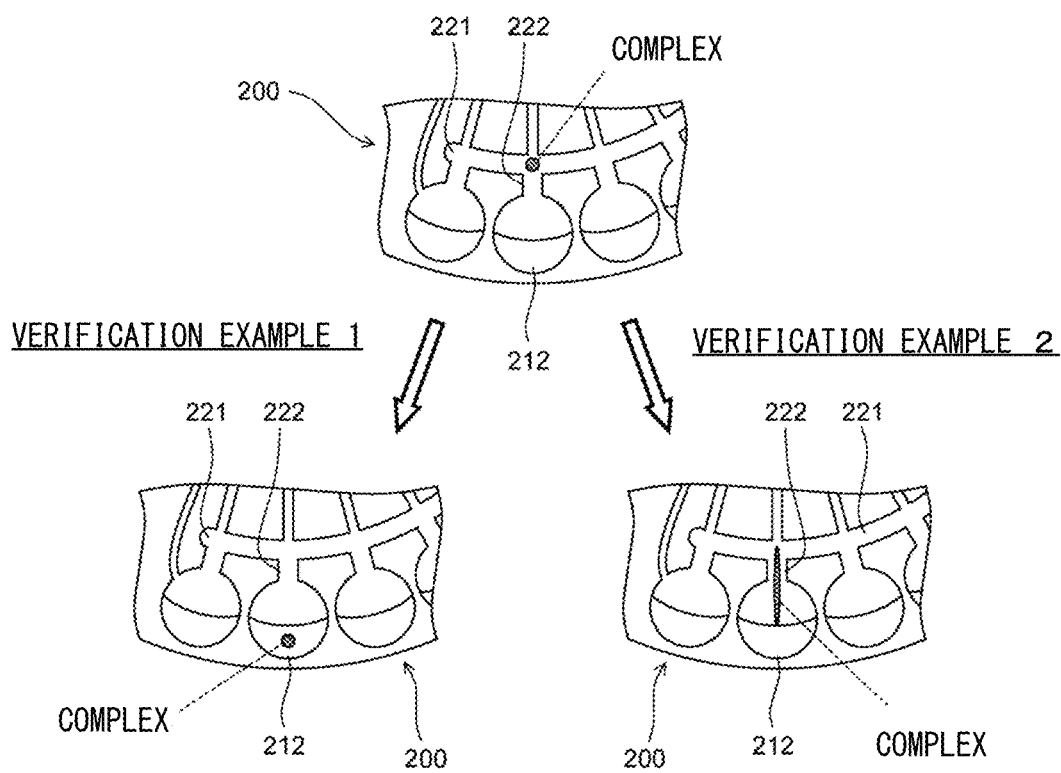
FIG. 18B schematically illustrates complex transferring states according to verification examples 1, 2 of Embodiment 1.

The inventors took a photograph representing a state where the complex was transferred, and confirmed that the complex was actually left behind. FIG. 18B conceptually illustrates the actual photographs that were taken by the inventors.

As shown in the upper illustration in FIG. 18B, in both of verification examples 1 and 2, the complex was positioned in the connecting portion between the region 222 connecting to the chamber 212, and the region 221 in exactly the same manner. In verification example 1, the complex in the state shown in the upper illustration of FIG. 18B was transferred from the connecting portion into the chamber 212 by the magnet 120 as shown in the lower left illustration of FIG. 18B. However, in verification example 2, the complex in the state shown in the upper illustration of FIG. 18B was transferred by a centrifugal force, and the complex was thus left between the connecting portion and the chamber 212 as shown in the lower right illustration of FIG. 18B. Thus, when the complex is left behind, an amount of complex that finally reaches the chamber 216 is reduced. When the complex is left behind, reaction based on a desired amount of the complex does not occur in the chamber. Therefore, an amount of light that is finally generated by reaction in the chamber 216 is reduced.

The above-described experiments indicate that it is preferable that, when the complex is transferred, the magnet 120 is moved relative to the cartridge 200, and the complex is transferred by a magnetic force of the magnet 120. According thereto, it can be understood that, when the complex is transferred from the chamber to the connecting portion and when the complex is transferred from one of the connecting portions to another connecting portion as well as when the complex is transferred from the connecting portion into the chamber, the complex is preferably transferred by a magnetic force of the magnet 120. Therefore, when the complex is transferred by the magnet 120, the complex can be more assuredly transferred, and unintended reduction of the counted value based on detection by the light detector 144a can be prevented. Therefore, accuracy for analyzing a test substance by the analyzer 100 can be maintained high.

Embodiment 2

Figure 19A:
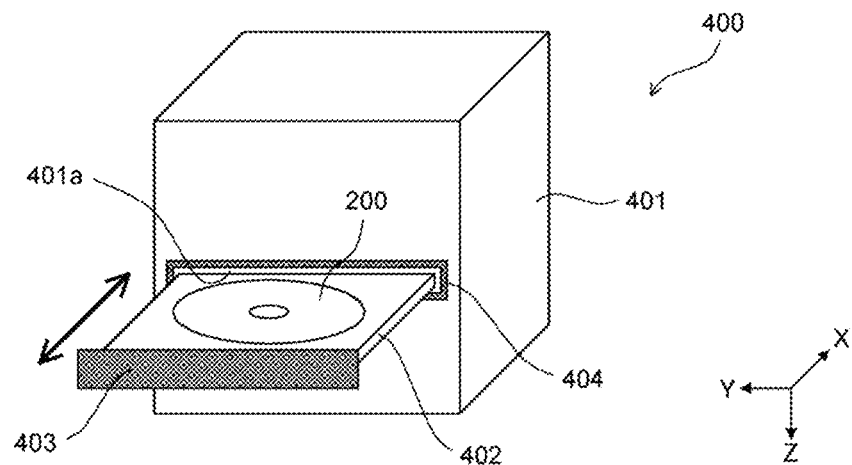
FIG. 19A is a schematic diagram illustrating an external structure of an analyzer according to Embodiment 2.

In Embodiment 1, as described with reference to FIG. 2A, the lid portion 102 is opened, and the cartridge 200 is placed at the analyzer 100. In Embodiment 2, as shown in FIG. 19A, the cartridge 200 is placed into an analyzer 400 by using a tray 402 that is movable to the outside through a hole 401a formed in the front surface of a casing 401 of the analyzer 400.

A light-shielding member 403 is mounted at the front end of the tray 402. The outer shape of the light-shielding member 403 is slightly greater than the hole 401a. An elastic member 404 having light-shielding properties is mounted near the outlet of the hole 401a. When the tray 402 is moved inward, the hole 401a is closed by the light-shielding member 403 and the elastic member 404. The other components of the analyzer 400 are substantially the same as described in specific example of structure for the analyzer 100 in Embodiment 1.

Also in Embodiment 2, similarly to Embodiment 1, the complex can be assuredly transferred, whereby accuracy for analyzing a test substance by the analyzer 400 can be maintained high. A dark space into which light does not come from the outside can be formed in the analyzer 400, whereby accuracy for detecting a test substance can be enhanced.

Embodiment 3

Figure 19B:
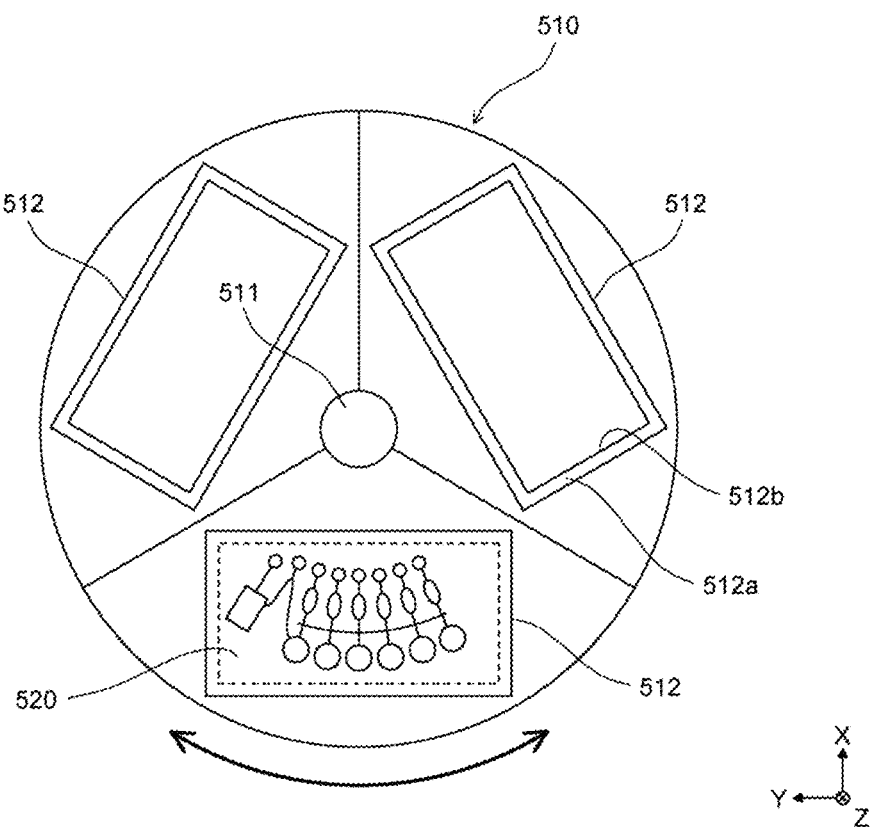
FIG. 19B schematically illustrates structures of a support member and a cartridge according to Embodiment 3 as viewed from thereabove.

In Embodiment 3, as shown in FIG. 19B, a support member 510 is disposed instead of the support member 177, and a cartridge 520 is used instead of the cartridge 200. The other components are the same as described in specific example of structure in Embodiment 1.

The support member 510 includes a hole 511 and three placement portions 512. The hole 511 is formed at the center of the support member 510. The support member 510 is mounted to the rotation shaft 311 through a predetermined member. Thus, the support member 510 can be rotated about the rotation shaft 311. The three placement portions 512 are provided in the circumferential direction. Each placement portion 512 has a surface 512a and a hole 512b. The surface 512a is formed so as to be one level lower than the upper surface of the support member 510. The hole 512b is formed at the center of the surface 512a, and penetrates through the support member 510 in the up-down direction. The cartridge 520 has a rectangular shape, and has the same structure as the cartridge 200.

When analysis is started, an operator injects a blood specimen into the cartridge 520, and places the cartridge 520 on the placement portion 512, as in the case of the cartridge 200 being used. As in Embodiment 1, the controller 301 drives the motor 171, the movement mechanism 130, and the detector 140. Thus, as in Embodiment 1, the complex in the cartridge 520 is assuredly transferred by the magnet 120. Therefore, as in Embodiment 1, accuracy for analyzing a test substance by the analyzer 100 can be maintained high. In Embodiment 3, the cartridges 520 can be placed on the three placement portions 512, respectively, whereby analysis can be performed simultaneously with the three cartridges 520.

Embodiment 4

In Embodiment 1, as shown in FIG. 1A, in order to change a position of the cartridge 200 and a position of the magnet 120 relative to each other in the radial direction, the movement mechanism 130 moves the magnet 120 in the radial direction. Meanwhile, in Embodiment 4, a movement mechanism 90 moves the cartridge 200.

Figure 20:
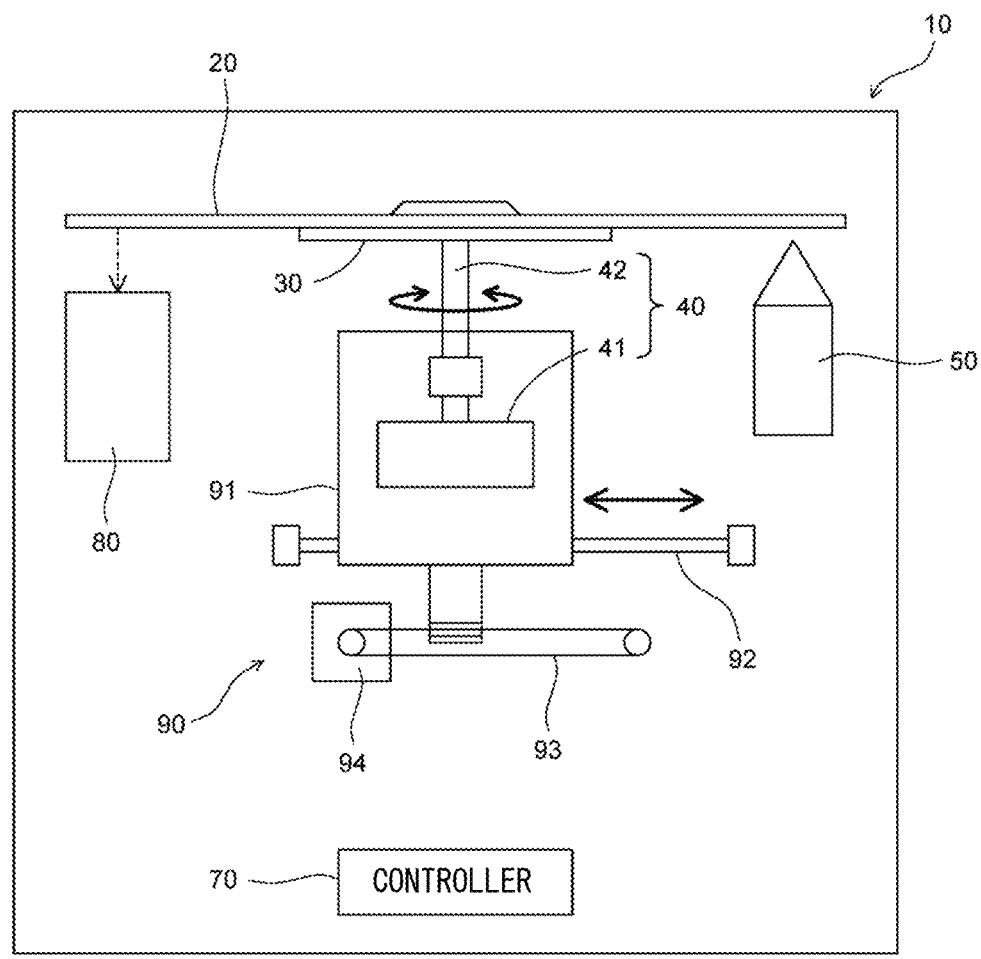
FIG. 20 is a schematic diagram illustrating a structure of an analyzer according to an outline of Embodiment 4.

As shown in FIG. 20, in Embodiment 4, the movement mechanism 90 is provided instead of the movement mechanism 130 as compared to the structure shown in FIG. 1A. The magnet 120 is fixed inside the analyzer 100. The other components are the same as described for outline structure of Embodiment 1.

The movement mechanism 90 supports the rotation mechanism 40 and allows the rotation mechanism 40 to move. The movement mechanism 90 includes a supporter 91, a rail 92, a belt 93, and a motor 94. The supporter 91 supports the rotation mechanism 40 from therebelow. The rail 92 extends parallel to a straight line that connects between the position of the magnet 120 and the position of the rotation shaft 42 in the horizontal plane, and guides the supporter 91. The belt 93 is extended on and between the drive shaft of the motor 94 and a pulley, and is disposed parallel to the rail 92. The lower end of the supporter 91 is connected to the belt 93. The motor 94 is implemented as a stepping motor. The motor 94 rotates the drive shaft, and thus moves the supporter 91 through the belt 93 along the rail 92. Therefore, the motor 94 is driven to move the cartridge 200 through the supporter 91, the rotation mechanism 40, and the support member 177.

In Embodiment 4, the cartridge 200 is moved parallel to the rail 92. Therefore, the position of the cartridge 200 located at the magnet 120 is changed in the radial direction. In Embodiment 4, similarly to Embodiment 1, the rotation mechanism 40 rotates the cartridge 200 in the circumferential direction. Therefore, also in Embodiment 4, similarly to Embodiment 1, since the magnetic particles can be moved, by the magnet 120, in the radial direction and the circumferential direction, the magnetic particles can be assuredly transferred.

In order to change the position of the cartridge 200 and the position of the magnet 120 relative to each other in the radial direction, both the magnet 120 and the cartridge 200 may be moved. However, when both of them are moved, the structure of the analyzer 100 becomes complicated. Therefore, one of them is preferably moved. In order to simplify the structure of the analyzer 100, as in Embodiment 1, only the magnet 120 is preferably moved.

Embodiment 5

In Embodiment 1, as shown in FIG. 2B, the chambers 211 to 216 each have a round shape. Meanwhile, in Embodiment 5, the chambers 211 to 216 each have a shape shown in FIG. 21A. The other components are the same as described in specific example of structure in Embodiment 1.

Figure 21A:
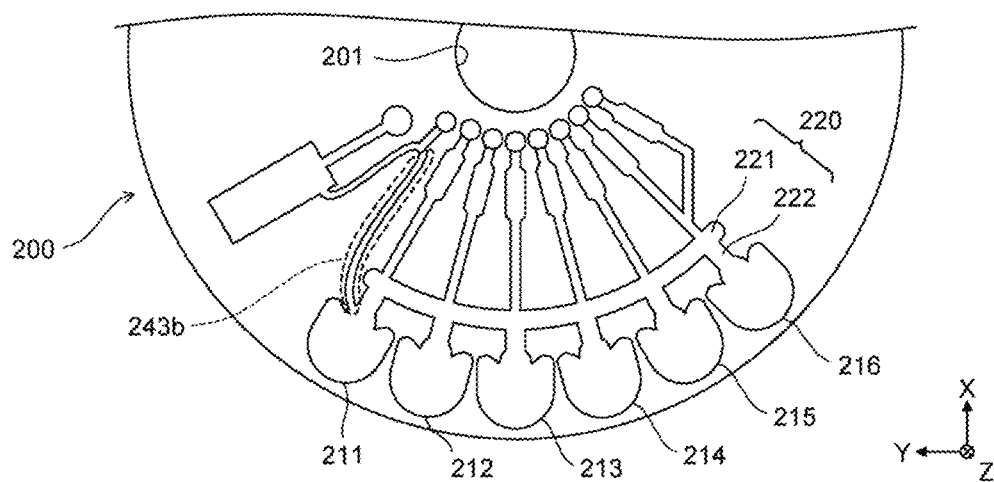
FIG. 21A is a schematic diagram illustrating a structure of a cartridge according to Embodiment 5 as viewed from thereabove.
Figure 21B:
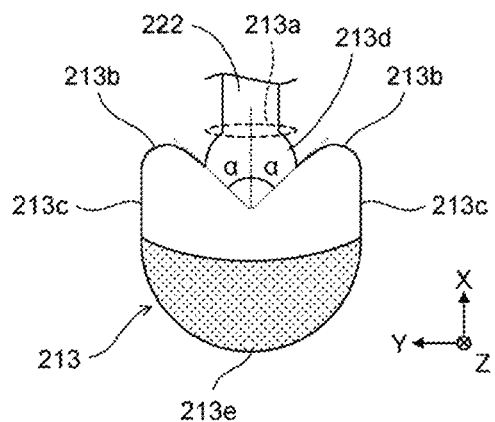
FIG. 21B is an enlarged schematic diagram illustrating a chamber of the cartridge according to Embodiment 5.
Figure 21C:
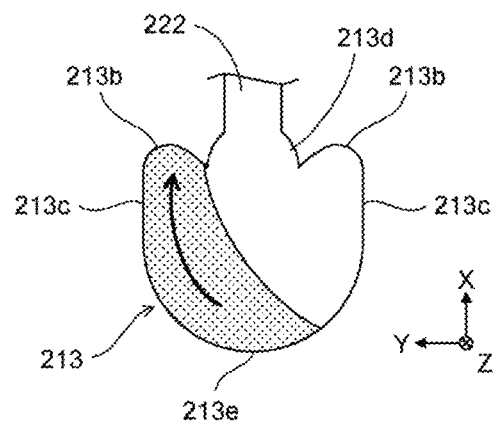
FIG. 21C is an enlarged schematic diagram illustrating the chamber of the cartridge according to Embodiment 5.

FIGS. 21B, 21C are each an enlarged view of a chamber 213 shown in FIG. 21A. In FIGS. 21A to 21C, the hole 201 of the cartridge 200 is positioned on the X-axis positive side of the chamber 213. That is, the rotation shaft 311 is positioned on the X-axis positive side of the chamber 213. The structures of the chambers 211, 212, and 214 to 216 are the same as the structure of the chamber 213, and the structure and the effect of the chamber 213 will be described.

As shown in FIG. 21B, the chamber 213 is shaped so as to be symmetric about the extension of the diameter of the rotation shaft 311. The chamber 213 is connected to the channel 220 on the rotation shaft 311 side. The chamber 213 includes protrusions 213b that protrude toward the rotation shaft 311 on both sides that sandwich a connecting position 213a connecting to the channel 220. In other words, the chamber 213 has the protrusions 213b that protrude in the X-axis direction, on the Y-axis positive side and the Y-axis negative side of the connecting position 213a. Each protrusion 213b is formed as a curved surface that protrudes toward the rotation shaft 311. An angle α between: the extension from the end portion on the connecting position 213a side of the protrusion 213b; and the extension, of the diameter of the rotation shaft 311, which passes through the center of the connecting position 213a, is less than 90°.

The chamber 213 has planar wall surfaces 213c connected to the protrusions 213b on both sides, respectively, which sandwich the connecting position 213a. The wall surfaces 213c connect to the end portions disposed on sides opposite to the connecting position 213a sides of the protrusions 213b. Specifically, each wall surface 213c extends in the radial direction as viewed in the Z-axis direction, that is, extends in the X-axis direction. The chamber 213 has, between the two protrusions 213b, a projection 213d that projects toward the rotation shaft 311. The channel 220 is connected to the projection 213d. The chamber 213 has an inner wall 213e disposed so as to be distant from the rotation shaft 311 in the radial direction. The inner wall 213e is arc-shaped as viewed in the Z-axis direction.

When the chamber 213 is structured as described above, the following effect is exhibited.

Also when, as described above, the cartridge 200 is rotated, and liquid in the chamber 213 is agitated by using a centrifugal force and Euler force, the two protrusions 213b act as barriers, and the liquid in the chamber 213 can be inhibited from entering the connecting position 213a connecting to the channel 220. That is, even if the liquid is moved in the chamber 213 by agitation, the leading end portion of the liquid in the chamber 213 is held in the chamber 213 by the protrusions 213b as shown in FIG. 21C. Thus, the liquid in the chamber 213 can be inhibited from entering the channel 220 during agitation.

Thus, liquid that flows from the chamber 213 into the channel 220 can be inhibited from entering another chamber, and causing undesired reaction in the chamber. An appropriate detection in the chamber 216 can be inhibited from becoming impossible due to washed liquid or the like containing impurities having flowed from the chamber 213 into the channel 220, and having entered the chamber 216 for detection. Thus, by flowing of liquid into the channel 220 during agitation being inhibited, the magnetic particles in the chamber 213 can be moved into the following chamber without leaving the magnetic particles behind, thereby performing appropriate detection.

Figure 21D:
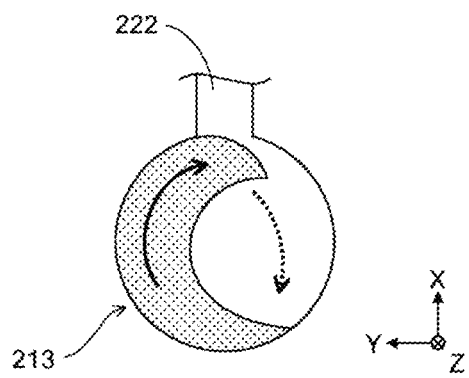
FIG. 21D is an enlarged schematic diagram illustrating a chamber of a cartridge according to a comparative example.

Even if liquid in the chamber 213 is greatly oscillated during agitation, the liquid in the chamber 213 is received by the protrusion 213b as shown in FIG. 21C, and the liquid is inhibited from further moving along the inner wall of the chamber 213. As shown in FIG. 21D, if the chamber 213 does not have the protrusions 213b, the liquid in the chamber 213 moves along the inner wall, and the leading end portion of the liquid in the flowing direction is curved in the X-axis negative direction by a centrifugal force as indicated by a dashed arrow, and hits against another portion of the liquid. In this case, the liquid bubbles due to the hitting of the liquid. However, as shown in FIG. 21C, when the protrusions 213b are formed in the chamber 213, the liquid in the chamber 213 is inhibited from moving forward along the inner wall, so that bubbling in the chamber 213 during agitation can be inhibited.

In a case where liquid is inhibited from entering the channel 220 and bubbling during agitation, a rotation speed of the cartridge 200 during agitation can be increased, and a degree of freedom for changing the rotation speed can be enhanced. Meanwhile, in a case where the rotation speed is thus controlled, heat generation from the motor 171 is increased. However, since the motor 171 is disposed outside the dark space 340 as described above, even when heat generation from the motor 171 is increased, the temperature in the dark space 340 can be inhibited from becoming unstable, and the measurement can be appropriately performed.

The chamber 213 has the planar wall surfaces 213c. Thus, when liquid is moved onto the wall surface 213c during agitation, change of the flow of the liquid can be increased as compared to a case where the wall surface is curved. Therefore, the liquid in the chamber 213 can be effectively agitated. As shown in FIG. 21D, when the wall surface is curved, the leading end portion of the liquid in the flowing direction is curved and is likely to hit against another portion of the liquid. However, since the wall surfaces 213c are formed so as to be planar, the state as shown in FIG. 21D can be inhibited from occurring. Therefore, liquid in the chamber 213 can be inhibited from bubbling during agitation.

Although the wall surfaces 213c are formed so as to extend in the radial direction, the wall surfaces 213c may extend so as to be tilted relative to the radial direction. However, in a case where the two wall surfaces 213c are tiled relative to the radial direction such that the end portions on the X-axis positive side are close to each other, although the liquid in the chamber 213 can be more effectively agitated, hitting in the liquid is likely to occur similarly as in the case shown in FIG. 21D. In a case where the two wall surfaces 213c are tilted relative to the radial direction such that the end portions on the X-axis positive side are distant from each other, although hitting in the liquid is less likely to occur, the liquid agitating effect in the chamber 213 is lowered. Therefore, as shown in FIG. 21B, the two wall surfaces 213c are preferably formed so as to extend in the radial direction.

Figure 21E:
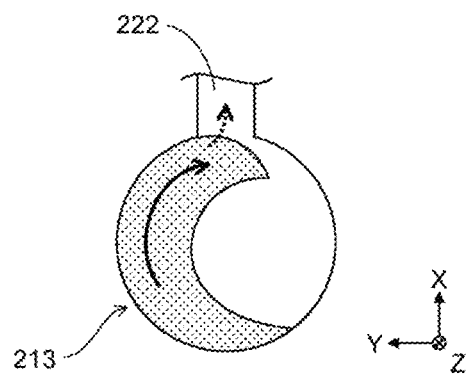
FIG. 21E is an enlarged schematic diagram illustrating a chamber of a cartridge according to a comparative example.

Even if liquid in the chamber 213 is greatly oscillated and flows over the protrusion 213b during agitation, the liquid that flows thereover is received by the projection 213d, and is less likely to enter the channel 220. As shown in FIG. 21E, in a case where the chamber 213 does not have the projection 213d, liquid that is greatly oscillated may enter the channel 220 as indicated by a dashed arrow. However, when the chamber 213 has the projection 213d, the liquid in the chamber 213 can be assuredly inhibited from entering the channel 220 during agitation.

Each protrusion 213b is formed as a curved surface that protrudes toward the rotation shaft 311. Therefore, the magnetic particles can be inhibited from being left in the protrusions 213b during agitation. Thus, the magnetic particles in the chamber 213 can be moved into the following chamber without leaving the magnetic particles behind. The chamber 213 is shaped so as to be symmetric about the diameter of the rotation shaft 311. Therefore, in both the Y-axis positive direction and the Y-axis negative direction, liquid can be inhibited from flowing into the channel 220 and bubbling. Since the angle α shown in FIG. 21B is less than 90°, the end portion of the protrusion 213b on the connecting position 213a side acts as a barrier, and liquid is assuredly inhibited from flowing into the channel 220 and bubbling during agitation.

The shape of the chamber 213 is not limited to the shape shown in FIG. 21B, and may be another shape. For example, the chamber 213 may have a shape as shown in any of FIGS. 22A to 22C.

Figure 22A:
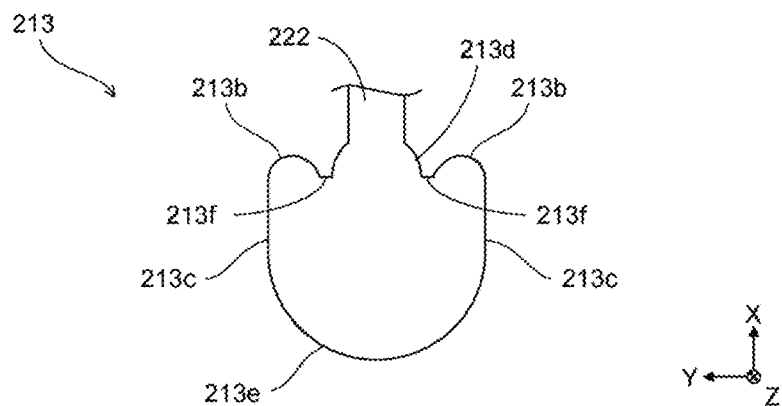
FIG. 22A is a schematic diagram illustrating a chamber according to modification of Embodiment 5.

In the chamber 213 shown in FIG. 22A, a straight line portion 213f is formed between each protrusion 213b and the projection 213d as compared to the structure shown in FIG. 21B. In this case, liquid received by the protrusion 213b is likely to flow toward the projection 213d along the straight line portion 213f due to surface tension. Therefore, as shown in FIG. 21B, the protrusions 213b and the projection 213d are preferably formed so as to be continuous with each other.

Figure 22B:
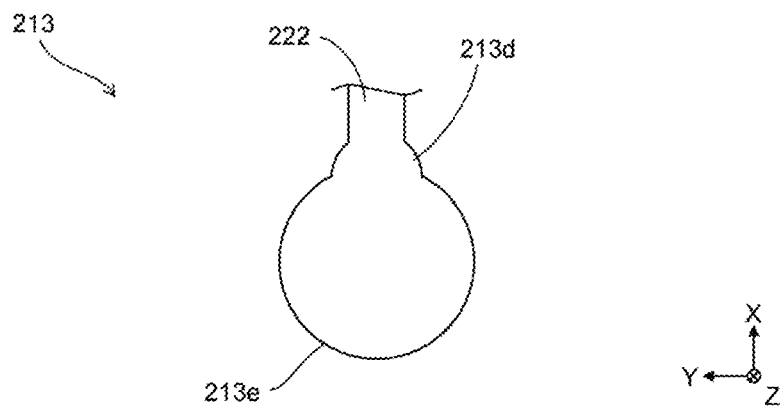
FIG. 22B is a schematic diagram illustrating a chamber according to modification of Embodiment 5.

In the chamber 213 shown in FIG. 22B, the protrusions 213b and the wall surfaces 213c are omitted as compared to the structure shown in FIG. 21B. In this case, when liquid in the chamber 213 is oscillated, the liquid in the chamber 213 is likely to enter the channel 220 as compared to the structure shown in FIG. 21B. However, as compared to the structure shown in FIG. 21E, the projection 213d is provided, and, thus, the liquid in the chamber 213 is less likely to enter the channel 220.

Figure 22C:
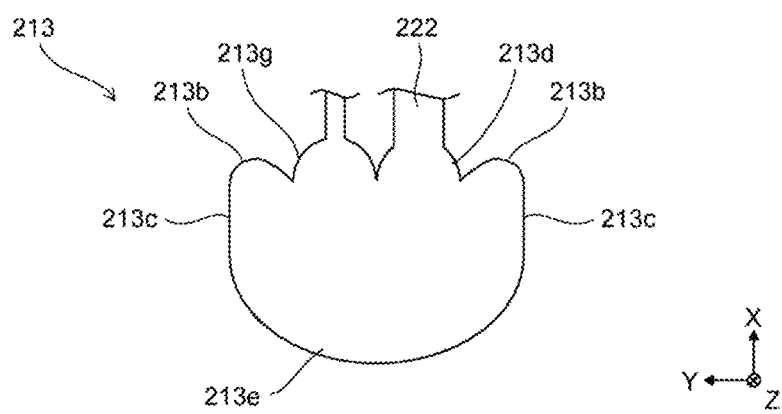
FIG. 22C is a schematic diagram illustrating a chamber according to modification of Embodiment 5.

In the chamber 213 shown in FIG. 22C, a protrusion 213g is further provided between the projection 213d and the protrusion 213b on the Y-axis positive side as compared to the structure shown in FIG. 21B. The protrusion 213g is connected to, for example, a flow path that allows air to pass therethrough, or a flow path other than the channel 220. When the structure shown in FIG. 22C is applied to the chamber 211, the projection 213d is connected to the channel 220 and the protrusion 213g is connected to the region 243b.

In the chamber 213 shown in FIG. 21B, a flow path that allows air to pass therethrough, or a flow path other than the channel 220 may be connected to the projection 213d. When the other flow path is connected to the projection 213d, forming of the cartridge 200 can be facilitated as compared to a case where the other flow path is connected to the region 222 of the channel 220.

Embodiment 6

Figure 23A:
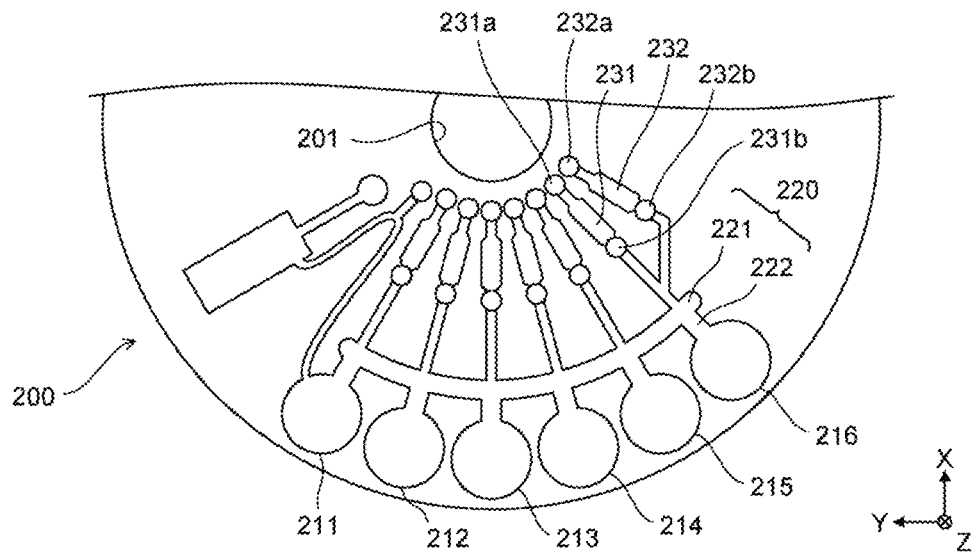
FIG. 23A is a schematic diagram illustrating a structure of a cartridge according to Embodiment 6 as viewed from thereabove.

In Embodiment 1, the liquid storage portions 231, 232 are each provided with the seal at only one position in the radial direction. Meanwhile, in Embodiment 6, the liquid storage portions 231, 232 are each provided with the seals at two different positions in the radial direction. Specifically, as shown in FIG. 23A, seals 231a, 231b are provided on the upper surfaces on the inner side and the outer side, respectively, in the radial direction, of the liquid storage portion 231. Seals 232a, 232b are provided on the upper surfaces on the inner side and the outer side, respectively, in the radial direction, of the liquid storage portion 232. In Embodiment 6, the pressing portion 195 is structured as shown in FIG. 23B to FIG. 24B. The other components in Embodiment 6 are the same as described in specific example of structure in Embodiment 1.

In Embodiment 6, when a reagent stored in the liquid storage portion 231 is transferred into a chamber disposed on the outer side of the liquid storage portion 231, the controller 301 firstly drives the motor 171 to rotate the cartridge 200, and causes the reagent in the liquid storage portion 231 to be positioned on the outer circumferential side in the liquid storage portion 231 by a centrifugal force. Subsequently, the controller 301 drives the pressing portion 195 to open the seal 231b positioned on the outer side of the liquid storage portion 231. Thus, the inside of the liquid storage portion 231 and the channel 220 are connected to each other. Subsequently, the controller 301 drives the pressing portion 195 to open the seal 231a positioned on the inner side of the liquid storage portion 231. Thus, the inner circumferential side portion of the liquid storage portion 231 and the outside of the cartridge 200 are connected to each other. The controller 301 drives the motor 171 to rotate the cartridge 200, and causes the reagent in the liquid storage portion 231 to be transferred into a chamber positioned on the outer side of the liquid storage portion 231 by a centrifugal force.

Also when the reagent stored in the liquid storage portion 232 is transferred into the chamber 216, the controller 301 performs the process similar to that described above. That is, the controller 301 causes the cartridge 200 to be rotated, causes the seal 232b to be opened, causes the seal 232a to be opened, and causes the cartridge 200 to be rotated in order, respectively.

In Embodiment 6, the reagent in the liquid storage portion 231 is enclosed in the liquid storage portion 231 by the seals 231a, 231b, and the reagent in the liquid storage portion 232 is enclosed in the liquid storage portion 232 by the seals 232a, 232b. Thus, the reagent in each of the liquid storage portions 231, 232 can be inhibited from flowing into the channel 220 or the chambers 211 to 216 before the cartridge 200 is used. When the reagent in each of the liquid storage portions 231, 232 is transferred into the chamber, the inner side portion and the outer side portion of each of the liquid storage portions 231, 232 are opened. Therefore, as compared to the structure in Embodiment 1, the reagent in each of the liquid storage portions 231, 232 can be smoothly transferred into the chamber.

Before the seal is opened, the reagent in each of the liquid storage portions 231, 232 is positioned on the outer circumferential side in advance. Thus, after the seal is opened, the reagent in each of the liquid storage portions 231, 232 can be smoothly transferred into the chamber positioned on the outer side. After the seals 231b, 232b on the outer side are opened, the seals 231a, 232a on the inner side are opened. Thus, the reagent in each of the liquid storage portions 231, 232 is not returned toward the inner side, and the reagent in each of the liquid storage portions 231, 232 can be smoothly transferred into the chamber positioned on the outer side.

Next, the pressing portion 195 of Embodiment 6 will be described.

The pressing portion 195 of Embodiment 6 includes a moving member 365 and a plurality of cam portions disposed in the moving member 365 for moving, in the pressing direction, pin members 366 for opening seals, respectively. The cam portions are disposed at different positions, respectively, in the direction in which the moving member 365 moves, in order to drive the pin members 366 in a predetermined order. Specifically, the pressing portion 195 is structured as shown in FIG. 23B to FIG. 24B.

Figure 23B:
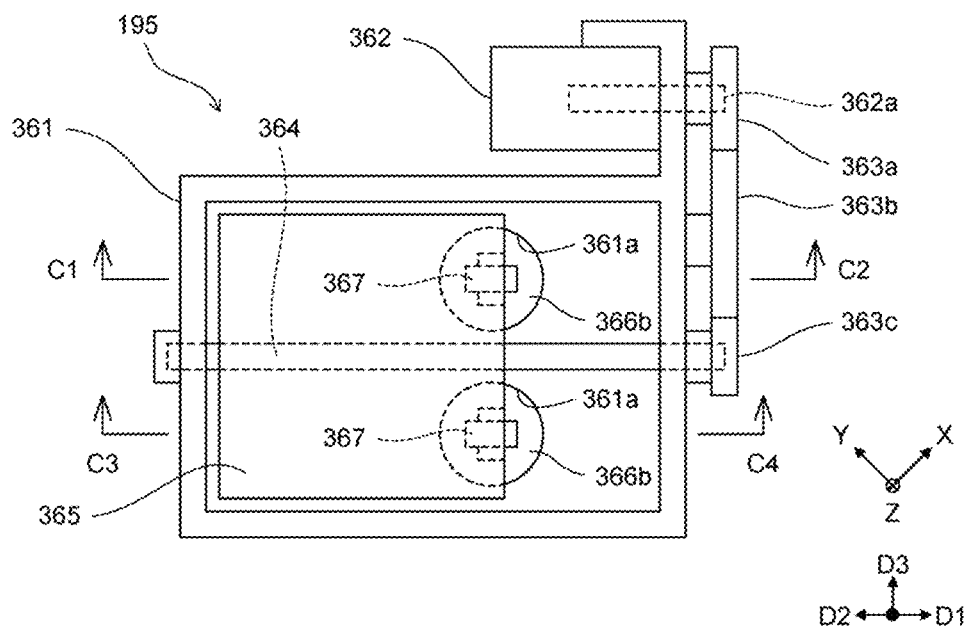
FIG. 23B is a schematic diagram illustrating a structure of a pressing portion according to Embodiment 6 as viewed from thereabove.
Figure 24A:
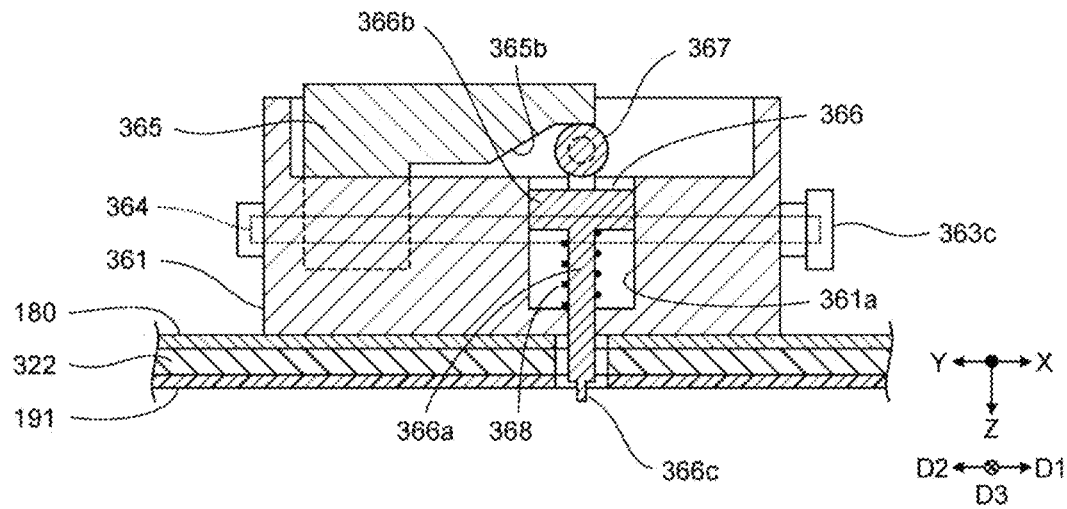
FIG. 24A is a schematic diagram illustrating a cross-section of the structure of the pressing portion according to Embodiment 6 as viewed from the side thereof.
Figure 24B:
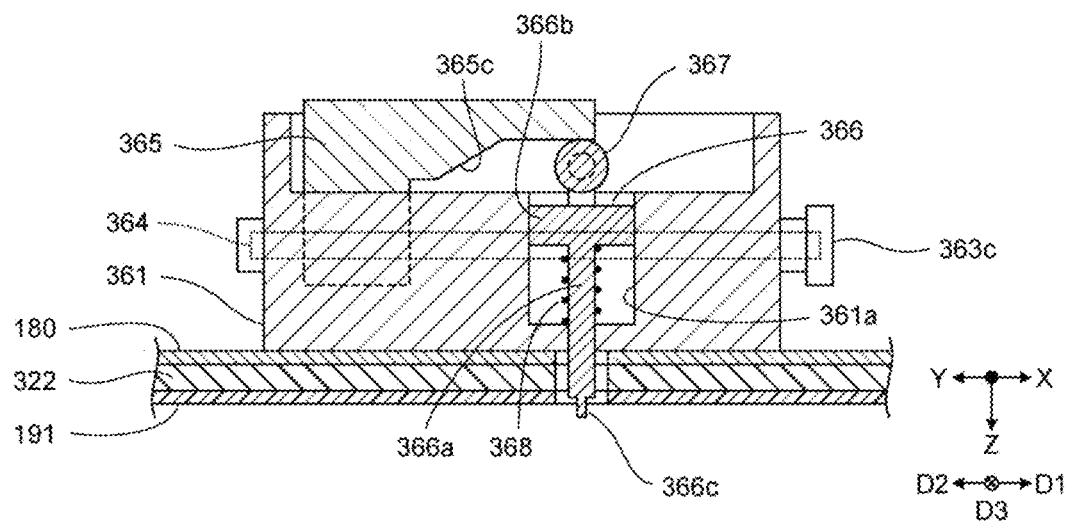
FIG. 24B is a schematic diagram illustrating a cross-section of the structure of the pressing portion according to Embodiment 6 as viewed from the side thereof.
Figure 25A:
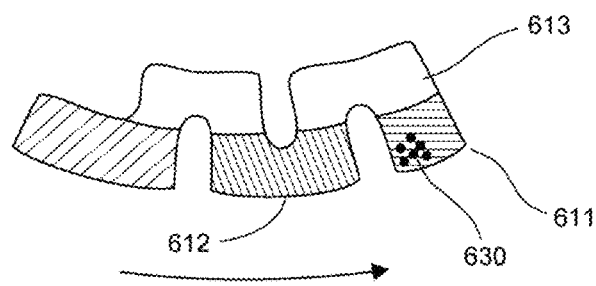
FIGS. 25A to 25D are schematic diagrams illustrating a structure of a related art.
Figure 25B:
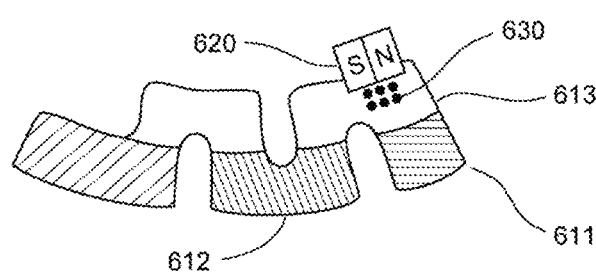
Figure 25C:
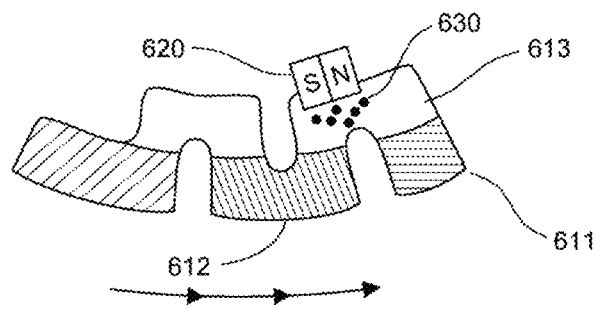
Figure 25D:
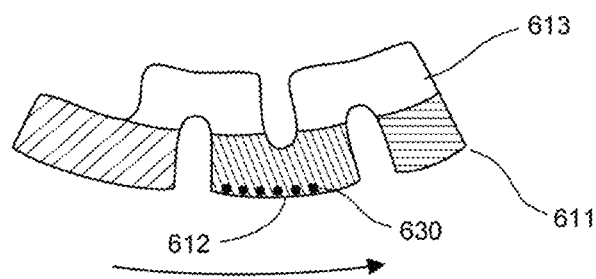

As shown in FIG. 23B, in Embodiment 6, as compared to the structure in Embodiment 1, the two pin members 366 are disposed in the radial direction. Specifically, the mounting member 361 has two holes 361a, and the pin members 366 and the rollers 367 are disposed at positions of the two holes 361a, respectively. FIG. 24A illustrates a cross-section of C1-C2 shown in FIG. 23B as viewed in the D3 direction. FIG. 24B illustrates a cross-section of C3-C4 shown in FIG. 23B as viewed in the D3 direction. As shown in FIGS. 24A, 24B, the pin members 366 are mounted at positions of the two holes 361a, respectively.

As shown in FIGS. 24A, 24B, on the lower surface side of the moving member 365, cam portions 365b, 365c are each formed as a plane tilted relative to the horizontal plane. The cam portion 365b is formed at the position corresponding to the roller 367 on the D3 direction side. The cam portion 365c is formed at the position corresponding to the roller 367 on the side opposite to the D3 direction side. The positions of the cam portions 365*b*, 365*c* are different from each other in the D1-D2 direction. Specifically, the cam portion 365*b* is disposed on the D1 direction side as compared to the cam portion 365*c*.

When the seals 231*a*, 231*b* of the liquid storage portion 231 are opened, the controller 301 causes the cartridge 200 to be rotated, to move the reagent in the liquid storage portion 231 toward the outer side, and thereafter causes the seals 231*a*, 231*b* to be positioned vertically below the pin member 366 on the side opposite to the D3 direction side, and vertically below the pin member 366 on the D3 direction side, respectively.

The controller 301 drives the motor 362 to move the moving member 365 in the D1 direction. In this case, when the moving member 365 is moved in the D1 direction in the states shown in FIGS. 24A, 24B, before the cam portion 365*c* contacts with the roller 367, the cam portions 365*b* contacts with the roller 367, and the cam portion 365*c* thereafter contacts with the roller 367. Therefore, the pin member 366 on the D3 direction side moves downward before the pin member 366 on the side opposite to the D3 direction side moves downward. Thus, as described above, the seal 231*b* on the outer side is opened earlier, and the seal 231*a* on the inner side is thereafter opened.

Thus, in a case where the cam portions 365*b*, 365*c* different from each other are provided on the lower surface of the moving member 365, and the pin members 366 are provided so as to correspond to the cam portions 365*b*, 365*c*, the seals 231*b*, 231*a* can be opened in order, respectively, simply by moving the moving member 365 in the D1 direction. For the seals 232*a*, 232*b* of the liquid storage portion 232, the opening process is performed in the similar manner. Also in this case, simply by moving the moving member 365 in the D1 direction, the seals 232*b*, 232*a* can be opened in order, respectively.

What is claimed is:

1. A method comprising:
    forming, on a magnetic particle, a complex of a test substance and a labeling substance in a cartridge, the cartridge comprising a plurality of chambers and a channel connecting the chambers;
    attracting the magnetic particle by a magnet;
    transferring the magnetic particle between the chambers, the transferring comprising:
    moving the magnet attracting the magnetic particle to move the magnetic particle between one of the chambers and the channel; and
    rotating the cartridge in a circumferential direction to move the magnetic particle through the channel while the magnetic particle is attracted by the magnet, wherein the magnet is moved in a direction different from the circumferential direction.
2. The method of claim 1, wherein
the magnet attracting the magnetic particle is moved in a radial direction of a circle in which a rotation shaft supporting the cartridge is centered.
3. The method of claim 1, wherein
the transferring comprises:
    (i) moving the magnet attracting the magnetic particle in a first direction and thereby moving the magnetic particle from a first chamber to the channel;
    (ii) rotating the cartridge and thereby moving the magnetic particle through the channel; and
    (iii) moving the magnet attracting the magnetic particle in a second direction and thereby moving the magnetic particle from the channel to a second chamber.
4. The method of claim 1, further comprising
detecting, with a detector, the test substance in the complex transferred from one of the chambers based on the labeling substance in the complex.
5. The method of claim 1, wherein
the magnet is arranged movably in a vertical direction relative to the cartridge, and the attracting comprises approaching the magnet to the cartridge in the vertical direction.
6. The method of claim 5, wherein
the magnetic particle is released from the magnet by moving away the magnet from the cartridge.
7. The method of claim 5, wherein
the magnet is arranged movably in a vertical direction and a horizontal direction relative to the cartridge,
the attracting comprises approaching the magnet to the cartridge in the vertical direction, and
the transferring comprises moving the magnet in the horizontal direction.
8. The method of claim 1, wherein
a plurality of complexes are formed on a plurality of magnetic particles, and
the method further comprising
dispersing the magnetic particles in one of the chambers by rotating the cartridge.
9. The method of claim 1, wherein
the labeling substance is reacted with a reagent in one of the chambers to emit a luminescence.
10. The method of claim 1, wherein
the complex is washed by a washing liquid in one of the chambers.

* * * * *